United States Patent [19]

James

[11] Patent Number: 5,383,939
[45] Date of Patent: Jan. 24, 1995

[54] SYSTEM FOR CONTROLLING ARTIFICIAL KNEE JOINT ACTION IN AN ABOVE KNEE PROSTHESIS

[76] Inventor: Kelvin B. James, 7955 98th Avenue, Edmonton, Alberta, Canada, T6A0B5

[21] Appl. No.: 804,264

[22] Filed: Dec. 5, 1991

[51] Int. Cl.6 ............................ A61F 2/64; A61F 2/70
[52] U.S. Cl. ........................................ 623/24; 623/44; 188/299; 188/317; 188/322.15
[58] Field of Search ................. 623/45, 24, 25, 26, 623/44; 92/110, 112, 143, 181 P; 188/299, 317, 322.15

[56] References Cited

U.S. PATENT DOCUMENTS 2,372,710 4/1945 Chisholm ........................... 92/181 P
5,062,856 11/1991 Sawamura et al. ..................... 623/24

FOREIGN PATENT DOCUMENTS 2623086 5/1989 France ................................. 623/25
0982527 2/1965 United Kingdom .................. 623/26
2244006 11/1991 United Kingdom .................. 623/25

Primary Examiner—David H. Willse
Attorney, Agent, or Firm—Terry M. Gernstein

[57] ABSTRACT

This invention relates to an above knee prosthesis which employs a hydraulic damper to passively regulate the angular velocity or rotation of the artificial knee joint. A programmed microprocessor recognizes common gait patterns from information received from bending moment strain and knee angle sensors on the prosthesis. The microprocessor, under the control of a rule-based program, reacts at various transition points in the gait by activating a motor which in turn adjusts a valve assembly in the damper. The valve assembly is capable of variably and separately damping the knee joint motion in each of flexion and extension at the same time. Gait is improved because of the improved extent of control of knee action. In addition, distinct routines such as stair descending and sitting down can also be practiced.

6 Claims, 26 Drawing Sheets

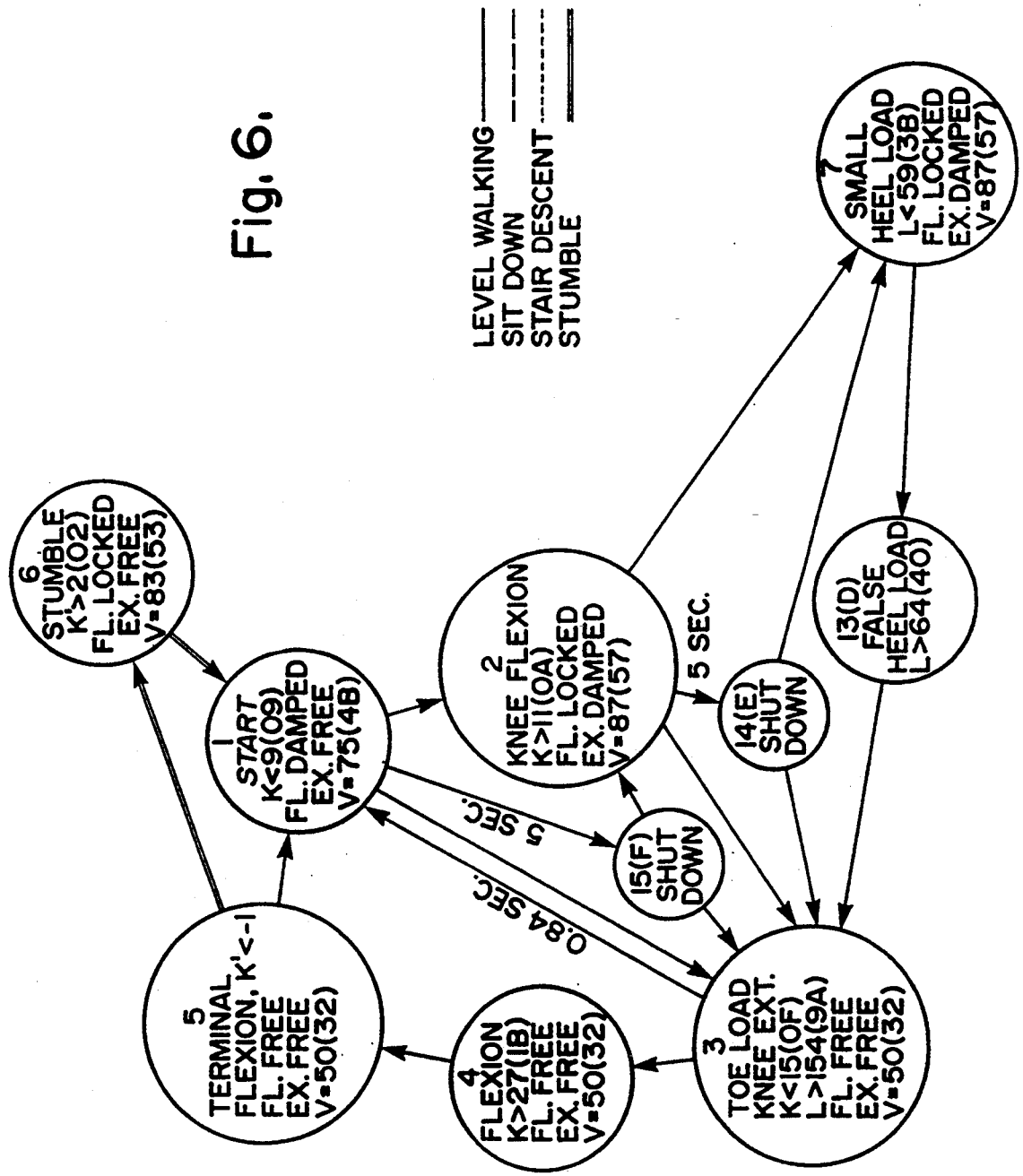

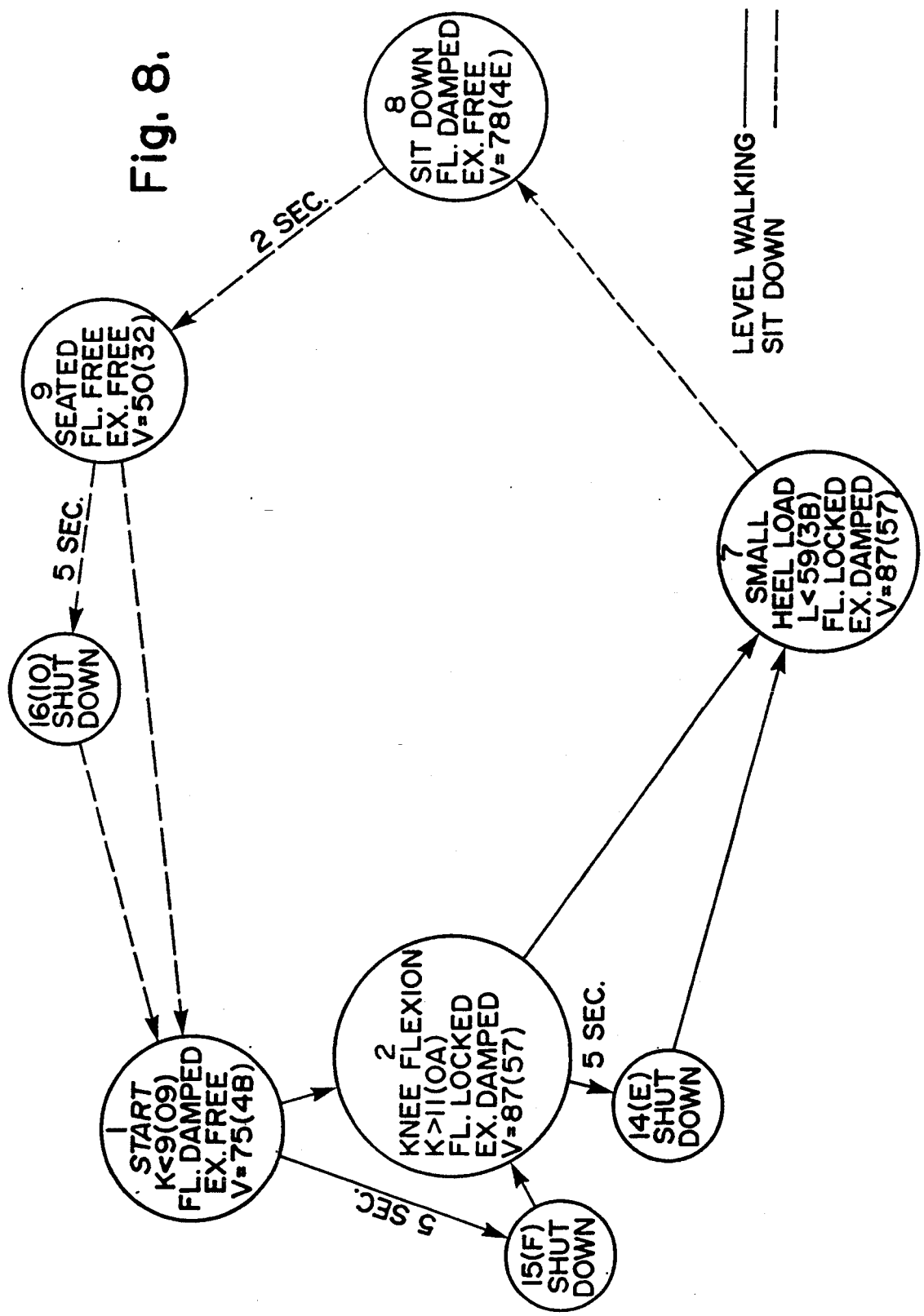

Fig. 33.

The core of the program is the Timer Interrupt Service Routine.
Every 20 miliseconds the timer interrupts and...

---

Timer Interrupt: (TimeInt @ 20 milisecond intervals)
 Get new A/D values into FIFO (first in, first out), discarding oldest values.
 Generate any required output to actuators.
 IF stop timer running, count down. On time-out, set halt flag, force
   battery cut-off rule to fire.
 IF Beep command active, execute time-outs as required, turn Beeper on/off.
 IF forced rule active, count down time. On time-out, force rule,
   goto END_OF_SCAN.
 IF not halted or not scanning already, scan rule table for executable rules.
 END_OF_SCAN: Return from timer interrupt

---

Scan: (of rules)
 For each active rule in MODE bit field
  IF rule preconditions exist and are met
  AND If digital conditions exist and are met
  AND If analog conditions exist and are met
  THEN fire rule, exit loop. (only one rule fires per timer interrupt).

---

FireRule:
 IF rule number not inhibited THEN generate required output.
  (Digital, Analog, Pulse, Mode change, Subroutine, Beep etc)
  Output current rule number to SPI port to permit external
   D/A monitoring of state changes.
  If a Forced Time exists, update FRCTIM counter.
  If rule is not special case (#0), update current rule value in memory.
   (for rule precondition tests).

---

A standard implementation of circular buffers is used for interrupt driven
input and output via a serial communications port on the microprocessor.
On each serial communications interrupt...

---

SERIAL INTERRUPT:
 IF Receiver interrupt THEN
  WHILE we do not have space in the input circular buffer, WAIT.
  Enque the received character, update in_pointer & counter.
 ELSEIF
  Transmitter interrupt THEN
   IF we have a character to send, send it, update out_pointer & counter.
  ELSE
   turn off transmitter interrupt since nothing left to send.
 Return from SERIAL INTERRUPT

SYSTEM FOR CONTROLLING ARTIFICIAL KNEE JOINT ACTION IN AN ABOVE KNEE PROSTHESIS

FIELD OF THE INVENTION

This invention provides a system for controlling the rotation of a knee joint of an above knee prosthesis. The system employs a microprocessor, responsive to lower leg bending moment strain and knee angle measurements originating from sensors on the prosthesis, to control a hydraulic damper through operation of a valve assembly associated with the damper, to thereby passively damp or resist the rotation of the artificial knee joint in each of flexion and extension.

BACKGROUND OF THE INVENTION

As previously stated, the present invention is used with an artificial leg or prosthesis worn by an above knee amputee.

There are today about 50 different above knee prosthetic devices on the market. Many of these prostheses involve:
- a socket for receiving and engaging the stump of the user;
- a knee bracket rigidly connected to the socket;
- a frame extending down from the bracket and being pivotally connected to the bracket by a horizontal shaft, said bracket, shaft and frame together combining to form an artificial knee joint;
- a pylon and artificial foot connected to the base of the frame; and
- means for controlling the knee joint by locking it to prevent it from buckling under load in the stance phase of a step, and freeing it in the swing phase of the step.

Now, the biological or natural knee joint is powered by the actions of muscles. Muscle has two elements. One is the active force developed by contraction and the other is variable stiffness. It has not been feasible to duplicate muscle contraction in leg prosthetics, due to limitations arising from weight and bulk. As a result, research has focused on implementing stiffness into the knee joint. This has usually involved switching the knee joint between one of two modes: locked up or free to rotate.

In recent years, researchers have sought improvement in controlling the action of the artificial knee joint, as a way to improve gait and enable the amputee to better deal with certain distinct actions, such as descending stairs or lowering into a sitting position.

A relevant patent in this regard is French patent 2623-086-A. This patent teaches providing a strain gage sensor on the frame between the knee joint and foot, to measure load. The electronic signals from the sensor are transmitted to a microprocessor which monitors the load measurement. When the load signal indicates that the swing phase of the step is ending and load is being applied to the leg, the microprocessor causes a motor or electromagnet to lock up the knee joint. When the stance phase is complete, the microprocessor instructs the actuator to release the knee joint, so that it is free to pivot in the swing phase.

Another relevant prior art reference is Russian patent SU1333-333-A. This patent teaches using a sensor at the knee hinge, to measure knee angle. Means lock or free the knee hinge in response to the knee angle measurements.

Another relevant prior art device is known as the Henschke Mauch S-N-S system for controlling an above knee prosthesis. This system incorporates a linear hydraulic damper for resisting rotation of the knee joint at a single damping rate in the stance phase. The damping rate can be varied by manual adjustment. When the knee joint is fully extended, the damper assumes a non-resisting mode. Otherwise stated, the system lacks automatic variation of damping and incorporates only two states, namely high resistance to flexion in stance phase and free rotation in swing phase.

If a knee joint is looked at as a simple hinge, there are two separate actions which can occur. In "flexion", the knee joint rotates to enable the upper and lower leg segments to move closer together. In "extension" the knee joint rotates in the opposite direction, the leg segments move apart and the leg straightens. For an artificial knee joint to more closely simulate a biological knee joint, it is necessary that control of resistance to knee rotation be applicable separately and variably in each of the flexion and extension modes. For example, it is desirable at the beginning of the stance (i.e. weight bearing) phase of the step to allow a small amount of knee flexion to occur and to then lock the knee against further downward flexion while simultaneously freeing the knee to extend as the leg straightens due to body action. So in the latter phase of this action, the knee joint is altered to being locked or stiff in flexion and free in extension, at the same time.

To applicant's knowledge, there is no artificial knee joint mechanism disclosed in the prior art which enables separate, simultaneous and automatic variable control of flexion and extension.

If such a mechanism could be devised, then a much more sophisticated control over the knee joint action could be implemented.

It is the object of the present invention to supply such a mechanism and to then incorporate it in an improved overall prosthesis.

SUMMARY OF THE INVENTION

The present invention relates to an on-board, computer-directed system adapted to provide improved automatic control of knee joint rotation in an above knee prosthesis (AKP) having upper and lower leg segments joined by the knee joint, said lower segment having a foot. In general, the system comprises:
- means for separately and variably damping or resisting each of flexion and extension rotational movements of the knee joint, said means preferably comprising a linear hydraulic damper adapted to simultaneously damp in both flexion and extension;
- electronic sensing means for measuring each of AKP knee angle and lower leg bending moment strain (which are respectively indicative of the angle between the leg segments and the position of the center of gravity of the user's body relative to the AKP foot) and emitting signals indicative thereof;
- actuating means, such as a servo motor, for adjusting the damping means to vary the resistance to rotation of the knee joint in at least one of flexion and extension; and
- programmed computer means for receiving the emitted signals from the sensing means, continuously establishing from said signals the state of the AKP in the course of a repetitive movement and activating the actuating means as required to vary damping to substantially simulate knee action. More particularly, the computer means is preferably adapted to do this by comparing the signals to stored threshold values which are indicative of pre-determined transition points between states of the AKP in the course of a movement, and, when the received signal values correlate with stored values, then causing the actuating means to vary damper resistance as required so that the AKP knee joint action substantially simulates natural knee action.

It will be noted that the invention involves separate variation of damping of AKP knee joint action in each of flexion and extension. "Damping" for this specification means resisting rotational movement of the knee joint. The resistance may be substantially complete, in which case the knee joint is substantially prevented from rotating in one or both of flexion and extension. The resistance may be partial, in which case the rate of rotation of the knee joint is restricted in one or both of flexion and extension. Or the resistance may be non-existent, in which case the knee joint is free to rotate in one or both of flexion and extension. Alternatively stated, the damper is adapted to control the rate of rotation of the knee joint in one or both of flexion and extension.

To enable such bi-directional damping, applicant has developed a novel damper incorporating a piston and means for controlling the piston. More particularly, the variable, linear, hydraulic damper comprises:

- a hollow closed cylinder filled with hydraulic fluid and having a cylindrical hollow piston adapted to slide longitudinally within the cylinder chamber;
- the piston preferably has axial rods extending from its ends, which rods project through sealed openings in the end walls of the cylinder. The piston further carries an exterior circumferential seal ring between its ends, for sealing against the side wall of the cylinder;
- a first aperture and check valve assembly, associated with a first end wall of the piston, enables fluid to enter the piston chamber from the first end of the cylinder chamber;
- a second aperture and check valve assembly, associated with the second end wall of the piston, allows fluid to enter the piston chamber from the second end of the cylinder chamber;
- a first pair of diametrically opposed ports extend through the piston side wall adjacent its first end, on one side of the seal ring;
- a second pair of diametrically opposed ports extend through the piston side wall adjacent its second end, on the other side of the seal ring;
- preferably, each first port is offset circumferentially from the second port on that side of the piston;
- preferably, each port is circumferential in position and slit-like in configuration;
- a valve preferably extends into the cylinder and piston chambers and is adapted to progressively reduce or increase the effective area of the first (or flexion) ports available for fluid flow and separately progressively reduce or increase the area of the second (or extension) ports;
- most preferably the valve comprises a rotatable shaft extending into the piston chamber in parallel relation to the cylinder axis, said shaft carrying a pair of radially protruding, diametrically opposed lobes, each lobe being adapted to substantially seal against the inside surface of the piston side wall, each lobe further being adapted, when the shaft is rotated, to progressively cover or uncover the adjacent flexion and extension ports, to thereby separately and simultaneously control flow area through the flexion and extension ports.

In use, one rod of the piston is connected to one segment of the AKP and the far end of the cylinder is connected to the other segment. For purposes of this description, it is assumed that the upper push rod of the damper piston is pivotally connected to the upper leg segment of the AKP and the lower end of the cylinder is pivotally connected to the lower leg segment. Therefore, in flexion the damper will contract and thus the piston will be driven downwardly in the cylinder by body load. In extension, the damper lengthens and the piston is pulled upwardly by body action. In the operation of the damper:

If the valve is positioned to enable flexion and if the piston is forced downwardly, thereby pressurizing fluid in the lower end of the cylinder chamber, fluid will flow upwardly through the lower check valve and extension ports, if open, into the piston chamber and will leave the piston chamber through the upper flexion ports—fluid will not leave the piston chamber through the extension ports (if uncovered) because there is no significant fluid pressure differential between the lower end of the cylinder chamber and the piston chamber;

If the valve is positioned to enable extension and if the piston is pulled upwardly, thereby pressurizing fluid in the upper end of the cylinder chamber, fluid will flow downwardly through the upper check valve and flexion ports, if open, into the piston chamber and will leave the piston chamber through the lower extension ports—again fluid will not leave the piston chamber through the flexion ports because there is no significant fluid pressure differential between the upper-end of the cylinder chamber and the piston chamber.

It will be noted that the damper design is characterized by the following attributes:

The valve can be adjusted to vary port areas and thus fluid flow rates to thereby vary resistance to knee joint rotation in either flexion or extension at the same time, thereby enabling variation of damping in both directions at the same time;

Because the ports are provided in diametrically opposed pairs, the valve does not get pressed against one side of the piston wall under heavy load and therefore does not seize up or become difficult to move—thus a small motor and shaft can be used to control the damper, which contributes to the compactness and lightness of the unit;

Because the damper is hydraulic, it is not significantly affected by wear and remains substantially consistent in its damping performance, thereby enabling the user to become accustomed to its "action" and to gain confidence in its performance. One could argue that the temperature of the hydraulic oil could vary and this would affect consistency of performance but this effect is minimized by using aircraft hydraulic fluid.

In a broad aspect, the damper design therefore involves providing:

- a pair of closed chambers (for example the two ends of the cylinder chamber);

means (for example the piston and cylinder) connected to the leg segments and forming two passageways (for example each formed by a check valve assembly, the piston chamber and a pair of the ports), for moving or pumping fluid from one end chamber to the other through one of the passageways when the leg segments are moving together and through the other of the passageways when the leg segments are moving apart; and means (for example the valve and port assembly) for regulating the flow of fluid through each passageway.

In another aspect of the invention, advantage is taken of the repetitive nature of leg actions. If, for example, one is walking along a level surface, there are patterns of knee angle and lower leg bending moment strain measurements which do not change significantly from step to step. By monitoring the two sets of signals and timing, the computer software can determine the stage or stages of AKP motion and can initiate appropriate changes in flexion and extension capability. If there is deviation from the regular pattern, such as stubbing the AKP toe in the course of swing phase, the software can detect this change and initiate corrective action.

Thus the system incorporates a method for controlling the knee joint of an AKP, which can be stated in the case of level walking as follows:

storing, in a computer memory, threshold values of lower leg bending moment strain and knee angle, which values are indicative of the knee bending in stance phase, of anterior positioning of the center of gravity of body weight relative to the ankle or foot, and of swing phase, all in the course of a step along a level surface;

continuously sensing lower leg bending moment strain and knee angle during use of the AKP and producing electronic signals corresponding thereto;

comparing the signals against the stored threshold values and, when the signals substantially correlate with threshold values, actuating means for altering the rate of rotation of the knee joint in at least one of flexion and extension to enable the knee joint to flex at about the beginning of stance phase, to look the knee joint against flexion while enabling extension in the middle portion of stance phase, and to free the knee joint as it approaches the swing phase thereby substantially simulating natural knee action; and repeating the foregoing repetitiously.

By combining the sensing means, the damper having means which can simultaneously and separately control flexion and extension and the software based on the profiles of repetitive motion (said software being referred to as "rule-based"), a knee joint system has been evolved which is characterized by closely controlled, predictable responses. This results in the user gaining confidence in the system which then manifests itself in the form of a longer and more rhythmic gait. The software can react similarly whether the gait is fast or slow. And the software can be "fine tuned" to the particular user to gain further compatibility or altered to modify the operation of the AKP. In addition, the system is adaptable to controlling the knee joint in the course of actions other than level walking, such as stair descent and sitting.

From the foregoing, it will be understood that the invention utilizes programmed computer means for receiving the emitted signals from the sensing means, continuously establishing from said signals the state of the AKP in the course of a movement and activating the actuating means to vary damping to substantially simulate natural knee action. More particularly, the programmed computer means is adapted to compare the emitted signals against stored threshold values indicative of transition points between states of a repetitive movement of the AKP and, when the signals substantially correlate with threshold values, to alter the rate of rotation of the knee joint in one or both of flexion and extension. Preferably, the stored threshold values are selected from the group consisting of the absolute and derivative values of knee angle and the position of the center of gravity of the user's body relative to the AKP foot, the duration from the last transition point and the possible future states in the course of the movement.

The invention described can be thought of as a machine which reacts to the amputee's movements, thus improving gait. Confidence in the machine is necessary for the amputee to take full advantage of the machine's capabilities. This confidence is developed by ensuring that the machine reactions are reproducible, step after step.

In order to obtain consistent and reproducible reactions, the invention takes advantage of the reproducible mechanics of the prosthesis during normal walking. As previously stated, during each step the knee goes through a pattern of movement which is basically the same, step after step. Also reproducible from step to step are the strains on the frame of the AKP, developed by the weight of the amputee, and the angle changes of the knee joint.

The repetitive nature of the signals is an important aspect of the success of the invention. This allows the prosthesis to have consistent man/machine interactions. The prosthesis is a tool used by the amputee to perform different tasks. If the performance of this tool is predictable and reproducible, then user confidence is gained.

In summary, the invention works on the principle that each step can be divided into segments or states and that a machine reaction can be developed for each segment, thus improving gait. The division of the step is carried out by first obtaining information from the prosthesis, conditioning this information with electronics and analyzing it with software, and then implementing machine reaction by separately and simultaneously varying resistance to flexion and extension rotation of the knee joint.

DESCRIPTION OF THE DRAWINGS

FIG. 6 is a diagram showing the states in level walking, with the appropriate state conditions shown;

FIG. 8 is a diagram showing the states in sitting down, with the appropriate state conditions shown;

FIG. 33 is a flow chart of the software and FIG. 34 is an interrupt service routine which is activated every 20 milliseconds.

DESCRIPTION OF THE PREFERRED EMBODIMENT

Figure 4:
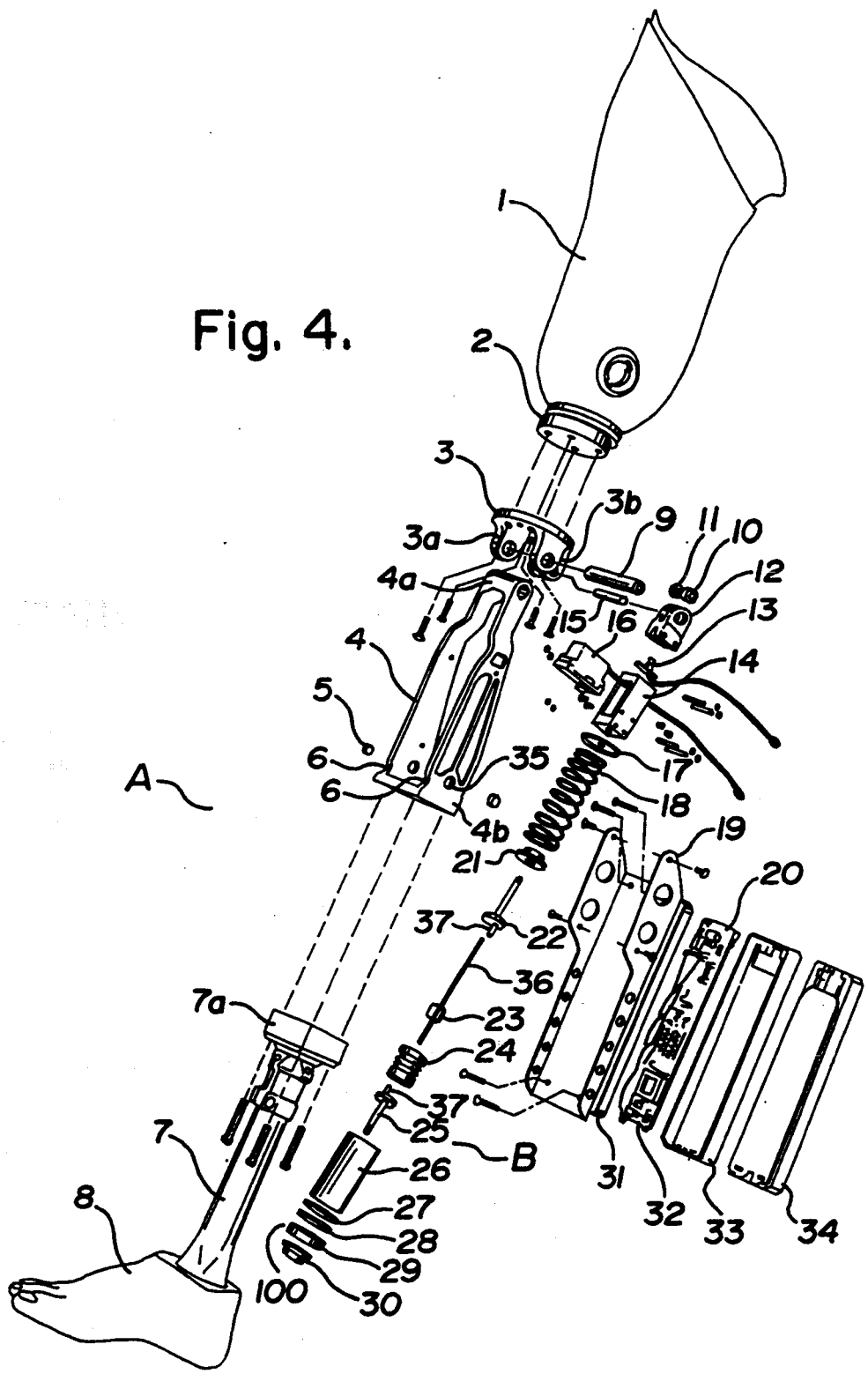
FIG. 4 is a perspective view of the prosthesis in exploded form.
Figure 4A:
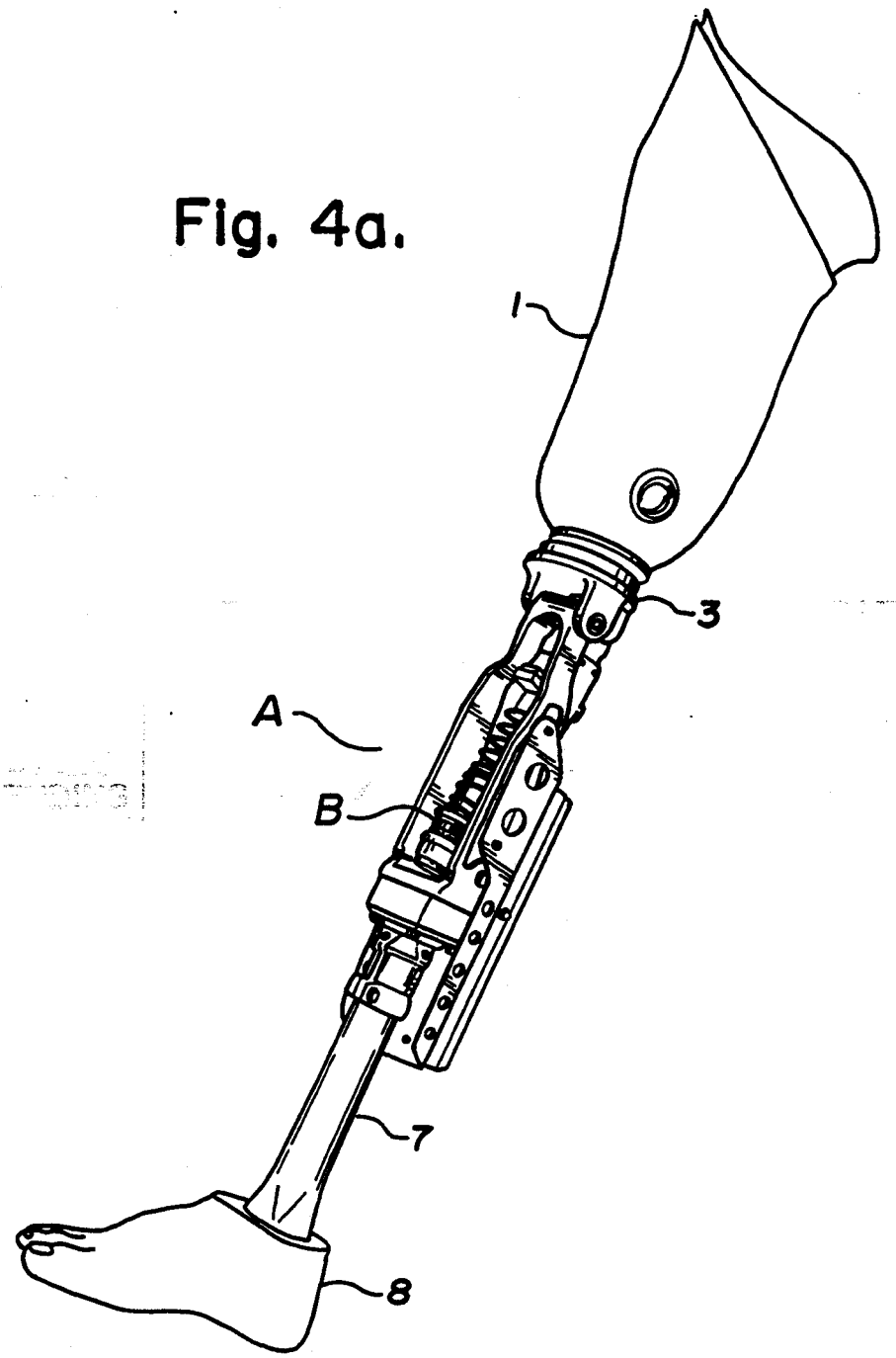
FIG. 4A is a perspective view of the prosthesis in assembled form.

Having reference to FIGS. 4 and 4a, the prosthesis A comprises a suction socket 1 which is custom fabricated to closely fit the stump of the amputee and to cling to it by suction. An adjusting plate 2 is attached to the base of the socket 1. A knee bracket 3 is secured by screws to the adjusting plate 2. The knee bracket 3 has apertured shaft supports 3a, 3b for receiving, supporting and affixing the main knee joint shaft 9 and the damper shaft 15 respectively. A frame 4, having a bearing 4a at its upper end, is rotatively mounted to the knee bracket 3 by the main shaft 9, which extends through the bearing 4a. The frame 4 is therefore free to rotate or pivot on the fixed main shaft 9. At its lower end, the frame 4 forms a rectangular socket member 4b for receiving a rectangular block 7a which is clamped to the upper end of the foot pylon 7. Screws secure the pylon block 7a to the frame socket member 4b. A foot 8 is secured to the lower end of the pylon 7.

An upper bearing housing 12 is mounted for rotation on the damper shaft 15. The damper shaft 15 is located to the rear of the main knee joint shaft 9, so that the shaft 15 and upper bearing housing 12 follow an arc relative to the shaft 9 when the knee bracket 3 rotates or pivots.

Figure 1:
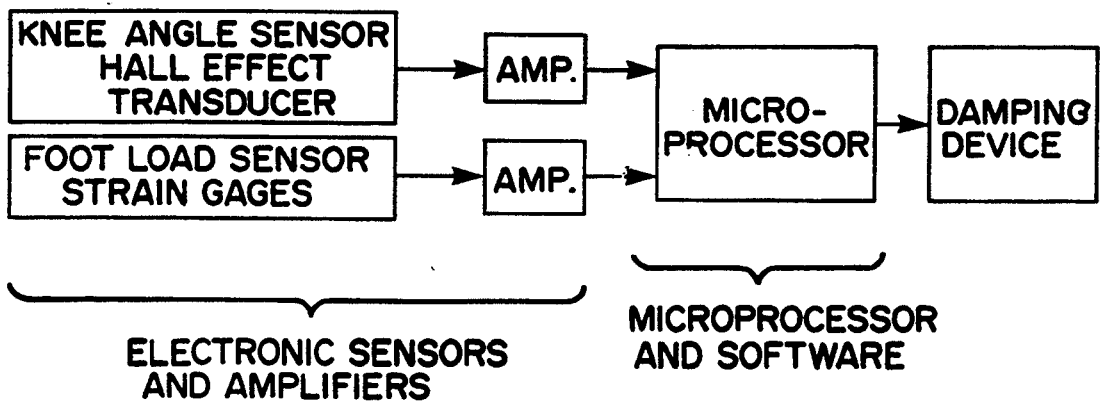
FIG. 1 is a block diagram showing the flow of information in the system.
Figure 2:
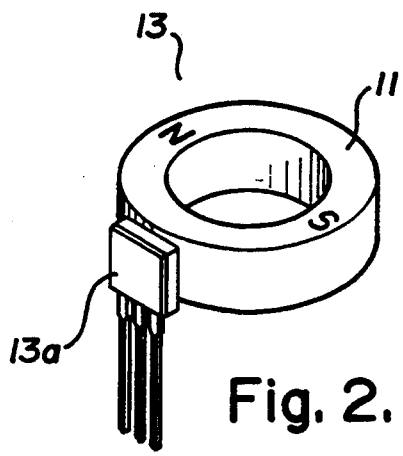
FIG. 2 is a perspective simplified view of the Hall effect sensor used for providing signals indicative of knee angle.

A Hall effect sensor 13, shown in FIG. 2, is provided to monitor the change in knee angle or knee joint rotation. The sensor 13 used is available from Sprague Electronics and is designated as model UGN-3503U. This sensor 13 comprises a ring magnet 11, which is fixed to the stationary damper shaft 15 of the knee bracket 3 by a ring magnet keeper 10. The sensor 13 further comprises a Hall effect transducer 13a, which is located in the rotatable upper bearing housing 12 and which is positioned facing the ring magnet 11. As knee joint rotation occurs, the bearing housing 12 moves around the damper shaft 15, causing the transducer 13a to move relative to the ring magnet 11.

Figure 3:
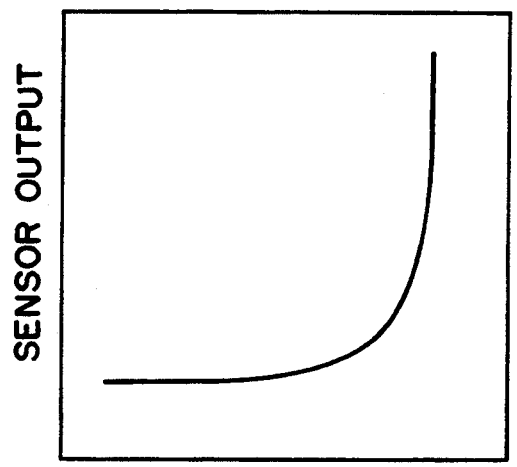
FIG. 3 is a plot of knee angle sensor output versus knee joint rotation.

The transducer 13a has a voltage output which is dependent on the magnet flux intensity (north or south pole) directly before it. Therefore, as the knee joint rotates, the output of transducer 13a changes. The signal from the linear Hall effect transducer is amplified to produce 0.5 volt with a knee joint extended fully and 4.5 volts with the knee joint flexed fully. Included in the circuit is a gain adjustment and an offset control. Stated otherwise, the signal of the transducer 13a is lowest when the knee is straight and increases as the knee is bent. FIG. 3 shows a typical sensor voltage output with respect to knee angle after amplification.

Figure 5:
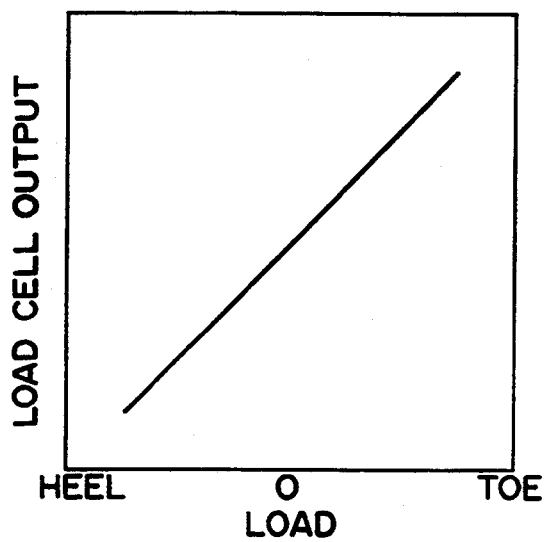
FIG. 5 is a plot of strain sensor output versus strain bending moment on the prosthesis.
Figure 31:
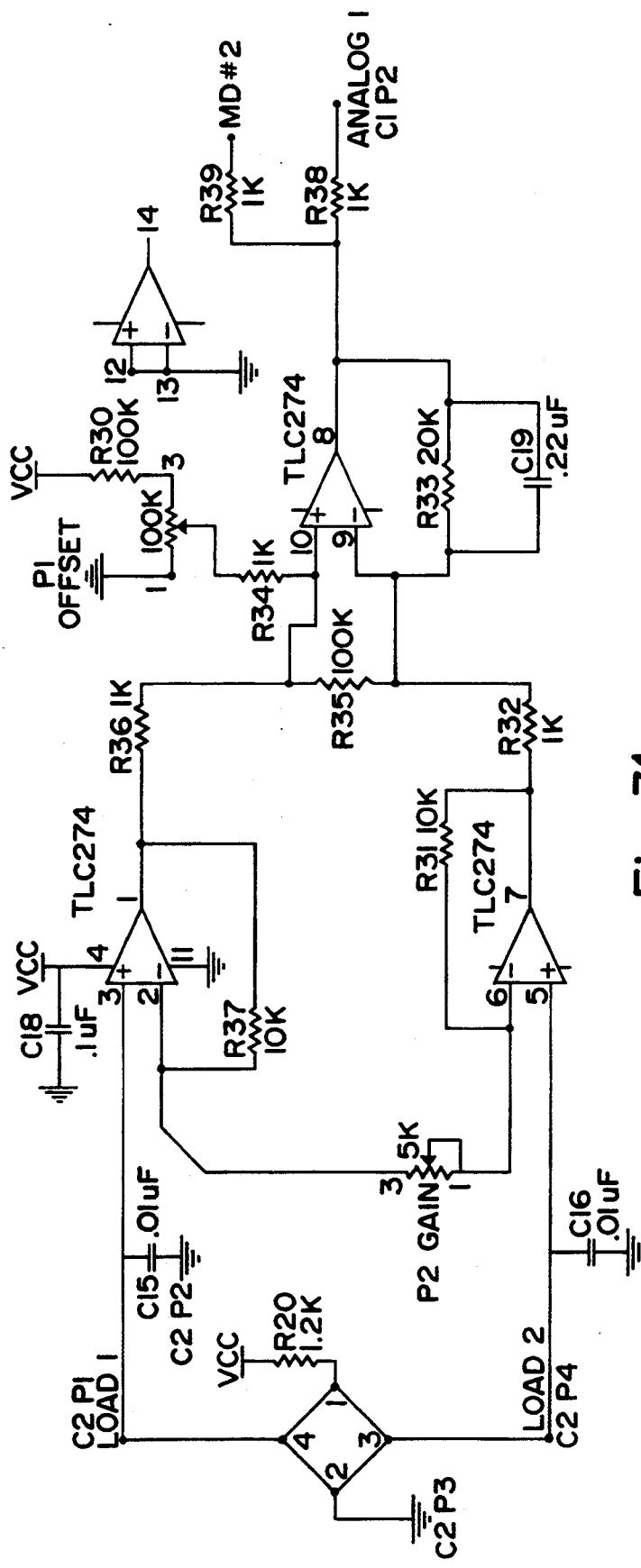
FIG. 31 is a diagram of the conditioning electronics for the bending moment strain sensor.
Figure 32:
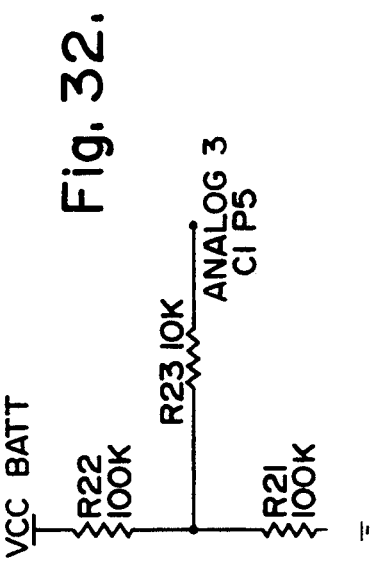
FIG. 32 is a diagram of the conditioning electronics for low battery detection.
Figure 34:
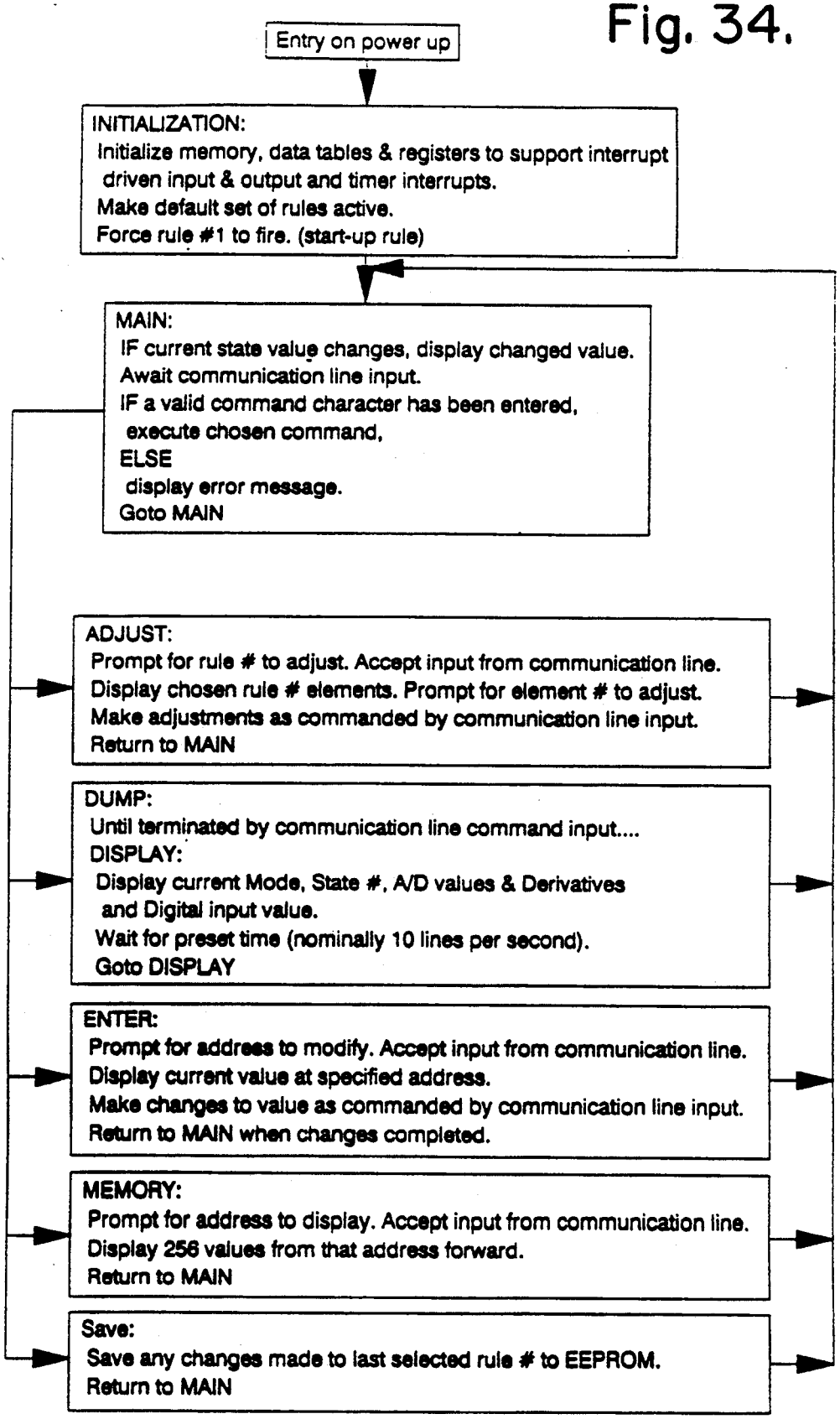
Figure 35:
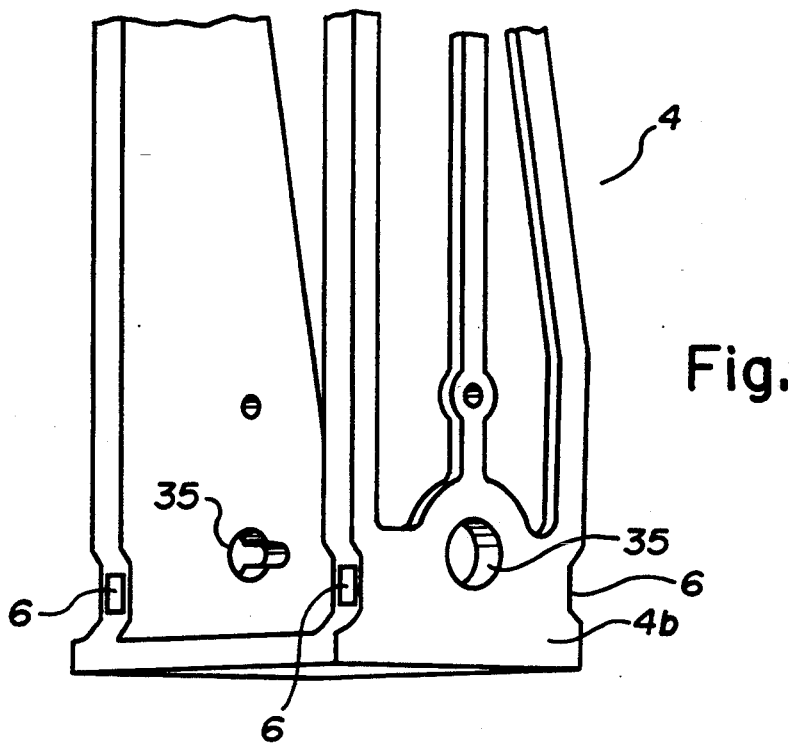
FIG. 35 is a perspective view showing bending moment strain gauge positioning on the base of the frame.

The forces on the foot 8 are established by measuring the bending moment strain of the frame 4. This is done using foil strain gauges 6 available from Micro Measurements Group Inc., Raleigh, N.C. under designation CEA-06-062 UW-350. Four gauges 6 are used, two at the front and two at the rear of the frame 4, located between the frame apertures 35 and the base of the frame 4, to measure and differentiate between load on the heel and load on the toe of the foot 8. Stated otherwise, the strain measurement provides an indication as to whether the user body center of gravity is in the anterior, centered or posterior position relative to the AKP foot. The four gauges are arranged in a wheatstone bridge configuration to produce an electric signal which changes proportionally with bending moment strain. The wheatstone bridge configuration detailed in FIG. 31 is a standard arrangement for determining the resistance change of strain gauges. The output of the bridge is amplified by a differential instrumentation amplifier to produce an output signal of 0.5 volts when the heel is loaded fully and 4.5 volts when the toe is loaded fully. No load or similar load on the toe and heel produces 2.5 volts. Included in the circuit is gain adjustment and an offset adjustment. FIG. 5 shows a typical voltage output of the bridge with respect to foot loading after the signal is amplified. It will be noted that the load signal decreases as the heel is loaded and increases as the toe is loaded. From the foregoing it will be noted that the foil strain gauges 6 in a wheatstone bridge configuration provide sensing means for monitoring bending moment strain; the output of such sensing means provides an indication of the position of the center of gravity of the user's body relative to the AKP foot, A servo motor bracket 14 is secured to the base of the bearing housing 12. A servo motor 16 is mounted within the bracket 14. The motor used is available from Airtronics Ltd. under designation 94737.

An upper spring retainer 17 is mounted on the base of the servo motor bracket 14, for a purpose to be described.

A damper B is positioned between the servo motor bracket 14 and the base of the frame 4.

The damper B comprises a hollow cylinder 26, which is externally threaded. A lower spring mount ring 27 is threaded onto the outside surface of the cylinder 26, for a purpose explained below. A lower bearing mount ring 29 is also adjustably threaded onto the outside surface of the cylinder 26, at its lower end. The ring 29 has radially extending threaded bores 100, normal to its central axis, which fit lower bearing pins 5 which are threaded through apertures 35 in the base of the frame 4. Thus the base of the cylinder 26 is pivotally coupled to the base of the frame 4 by threading the pins 5 into the bores 100 of the ring 29. A lock ring 28, threaded onto the external surface of the cylinder 26, is tightened against the ring 29 to lock it in place.

Figure 25:
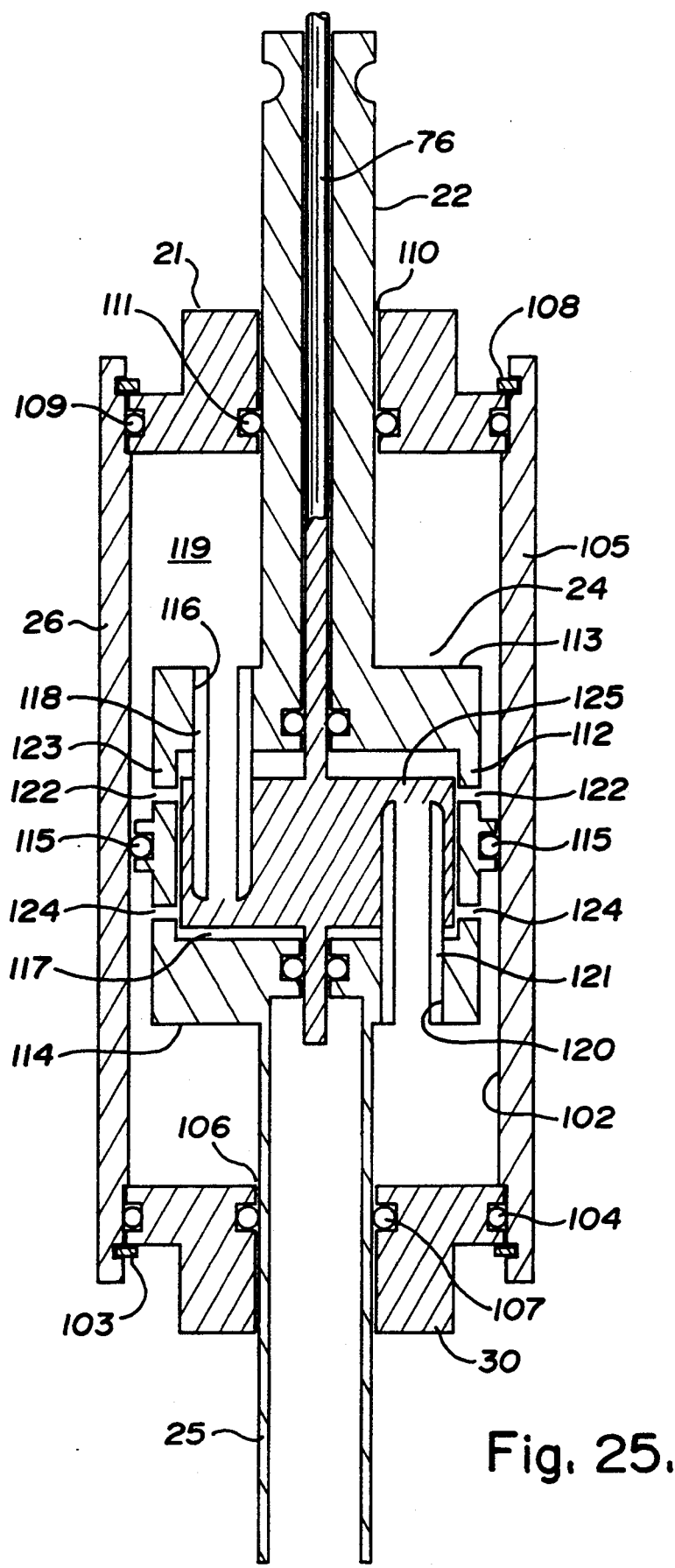
FIG. 25 is a side sectional view of the cylinder and piston.
Figure 26:
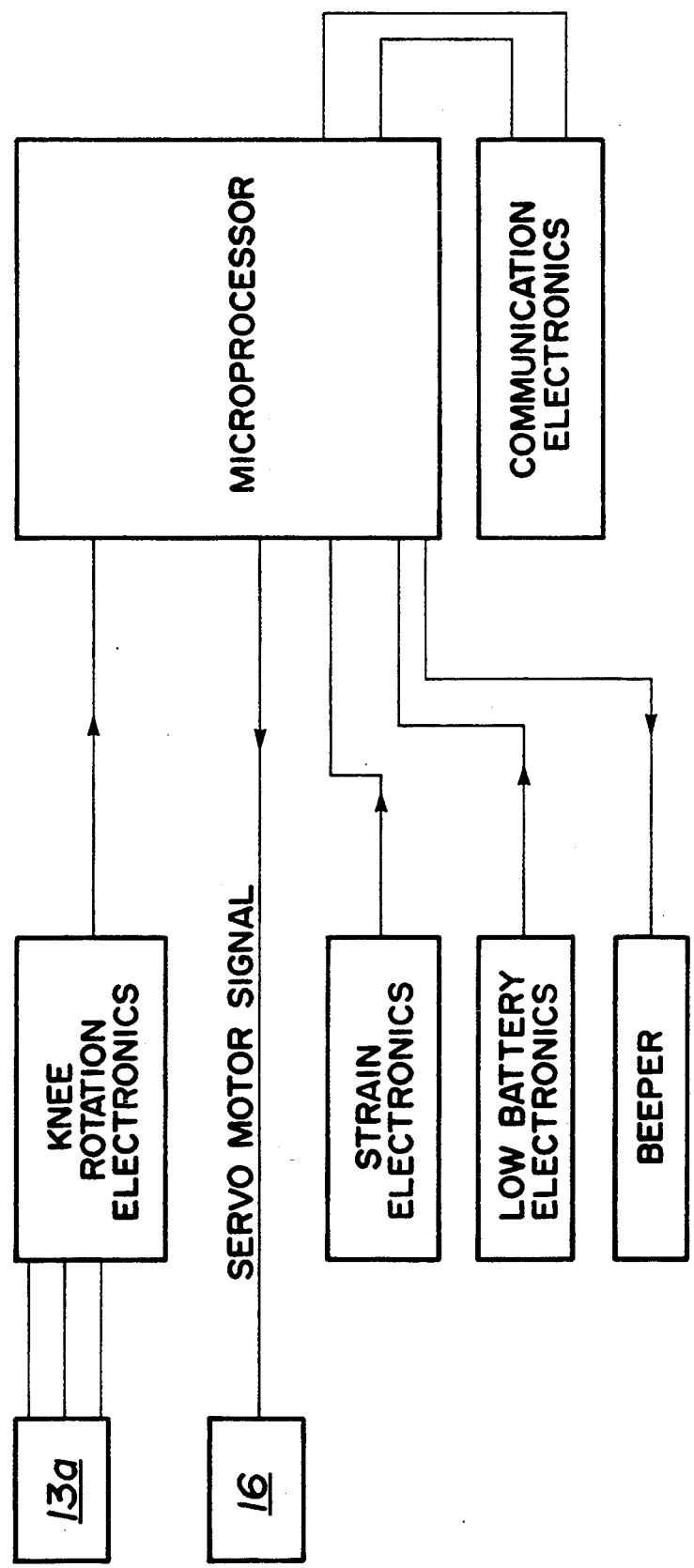
FIG. 26 is an overall circuit diagram of the system.
Figure 27:
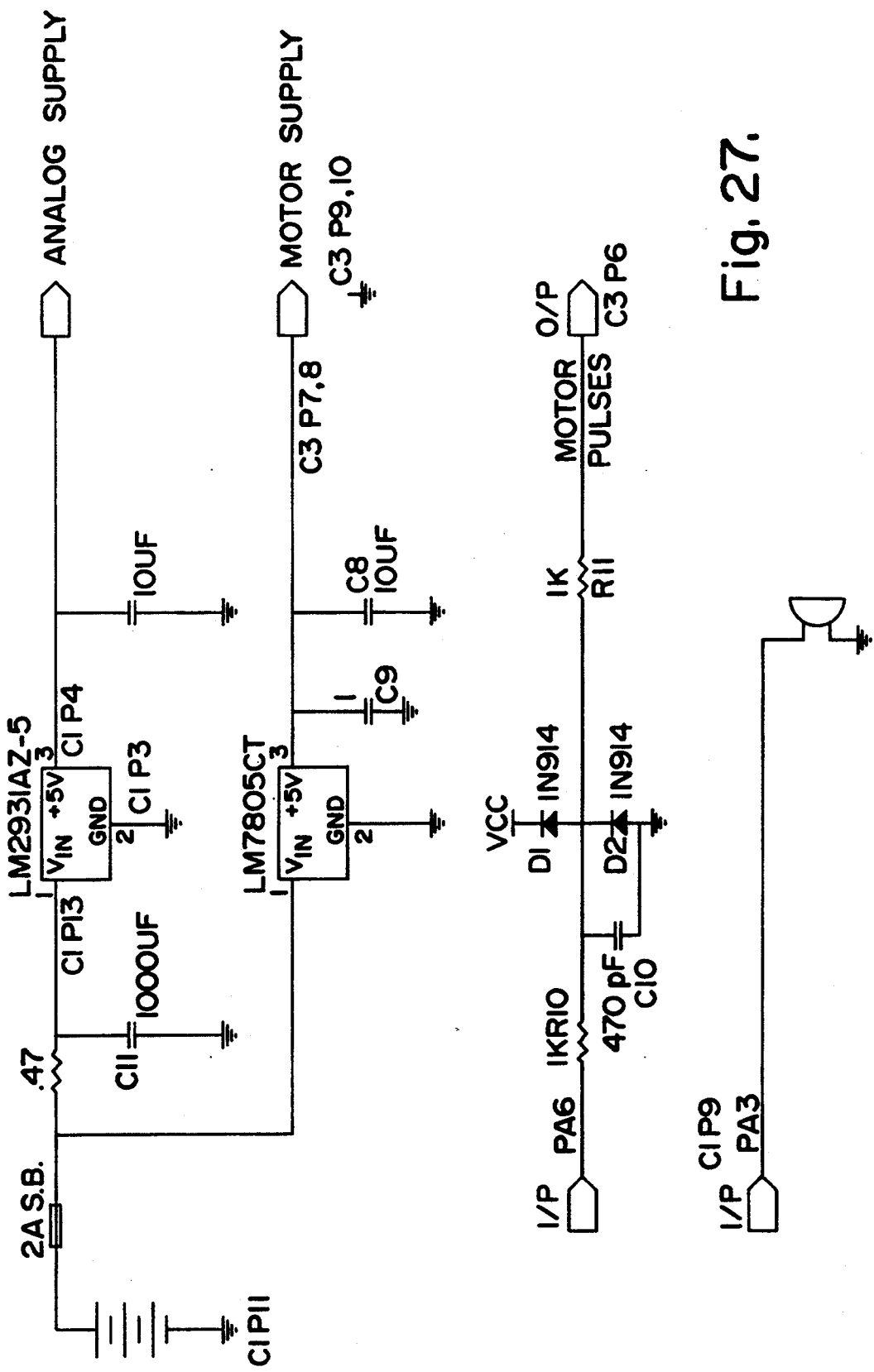
FIG. 27 is a partial diagram of the circuit showing power supply, connecting circuit between computer and motor, and beeper circuit.
Figure 28:
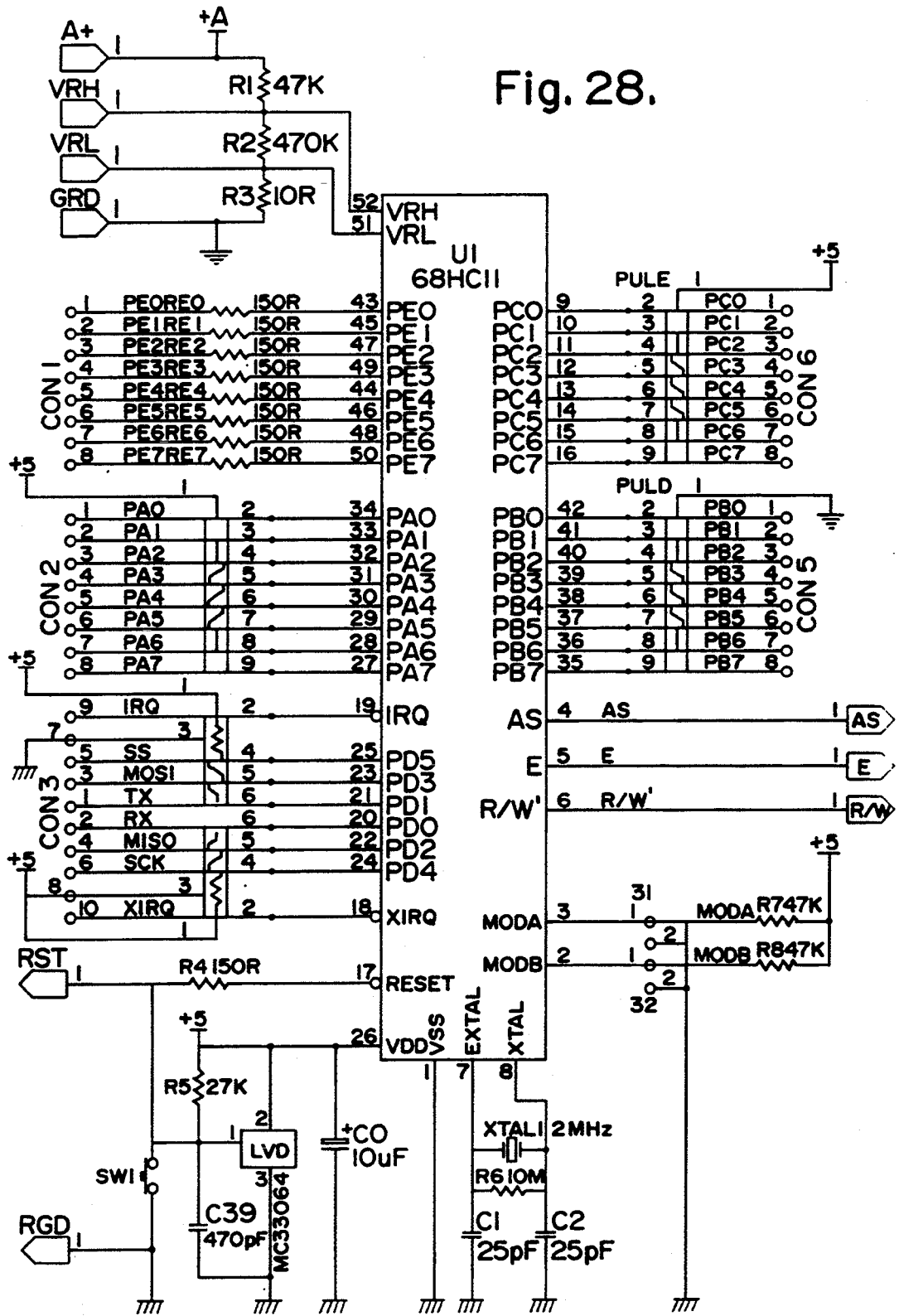
FIG. 28 is a diagram of the microprocessor chip.
Figure 29:
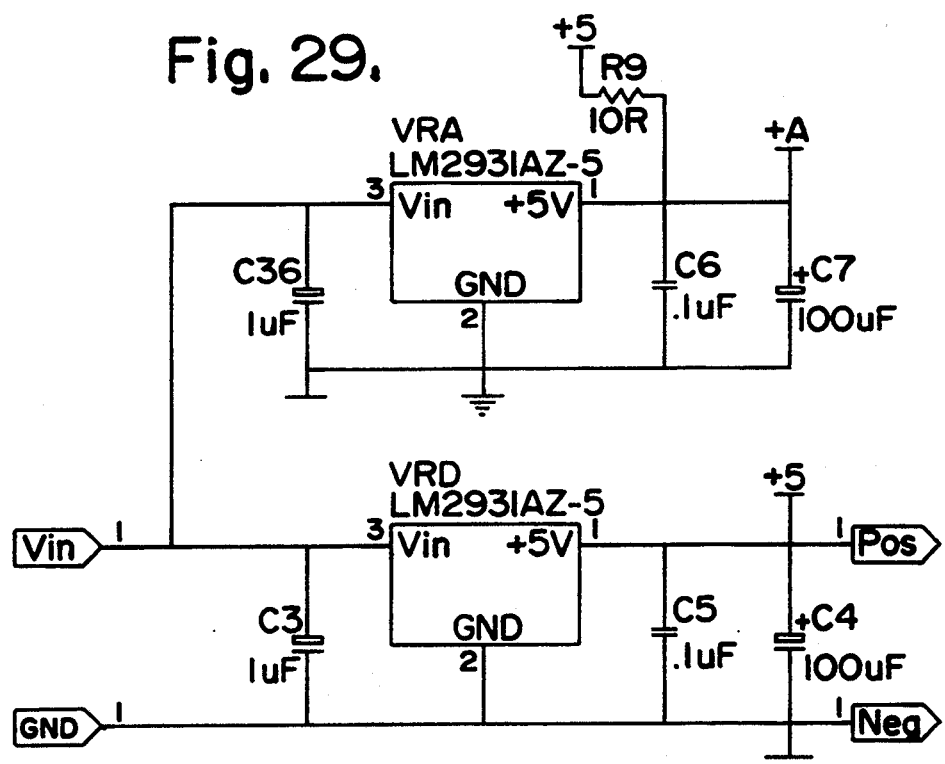
FIG. 29 is a diagram of the regulator for the analog to digital convertor located on the microprocessor chip.
Figure 30:
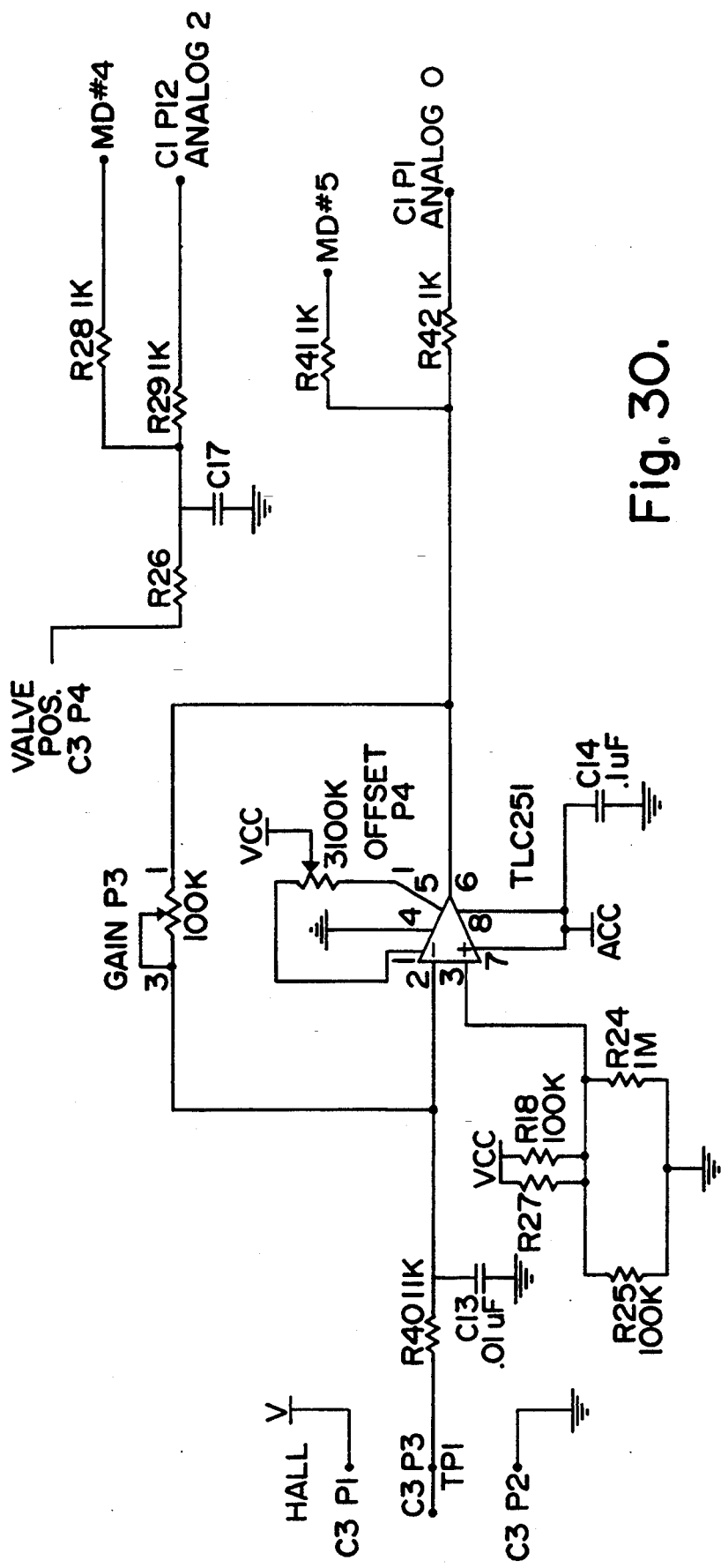
FIG. 30 is a diagram of the conditioning electronics for the Hall effect sensor.

A lower cap 30 fits into the bore 102 (see FIG. 25) of the cylinder 26 at its lower end and closes the bore. The lower cap 30 is held in place by a snap ring 103. The lower cap 30 carries a circumferential O-ring 104, for sealing against the side wall 105 of the cylinder 26. An aperture 106 is formed through the cap 30. An O-ring 107 is mounted in this aperture 106, sealing around the dummy push rod 25 of a piston 24.

At its upper end, the cylinder 26 has an upper cap 21 which fits into the cylinder bore 102 and is held in place by a snap ring 108. The upper cap 21 also carries a circumferential O-ring 109, for sealing against the side wall 105 of the cylinder 26. An aperture 110 is formed through the cap 21. An O-ring 111 is mounted in this aperture 110, for sealing around the push rod 22 of the piston 24.

The hollow cylindrical piston 24 is positioned in the cylinder bore 102. The piston 24 comprises an open-ended drum 112 having upper and lower end caps 113, 114 screwed thereinto. A push rod 22 extends upwardly from the upper end cap 113, through the sealed aperture 110 in the cylinder cap 21, and is secured to the servo motor housing 14. From the foregoing, it will be noted that the bearing housing 12, servo motor housing 14 and push rod 22 form a train of components connected to the damper shaft 15 and bracket plate 3. Thus as the socket 1 pivots about the main shaft 9, this rotational movement is converted into linear movement of the push rod 22 and piston 24.

A tubular spring 18 extends concentrically around the cylinder 26 between the upper spring retainer 17 and lower spring mount ring 27, for assisting the assembly to increase rate of knee extension during the swing phase of gait. This is useful in enabling increased speed of gait.

Figure 13:
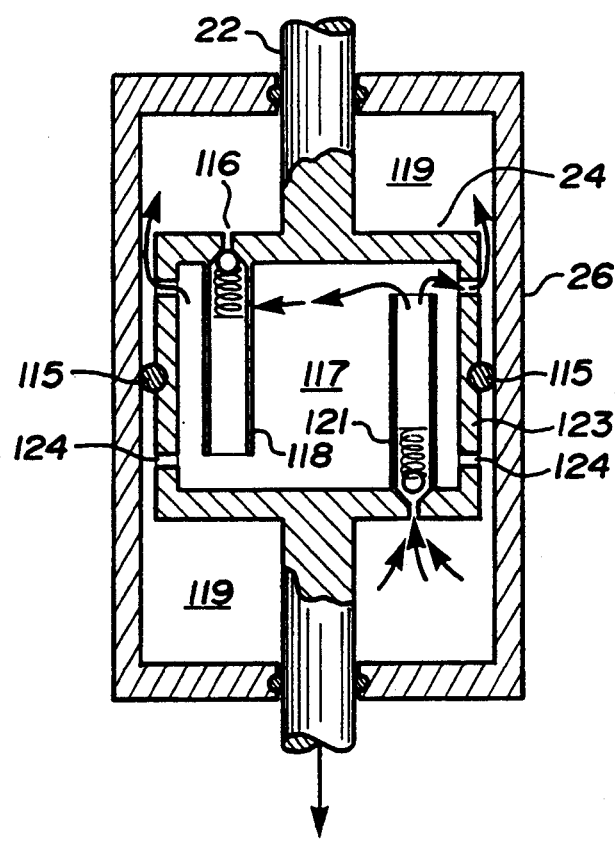
FIGS. 13 and 14 are simplified sectional side views showing the piston and cylinder in flexion and extension modes.
Figure 14:
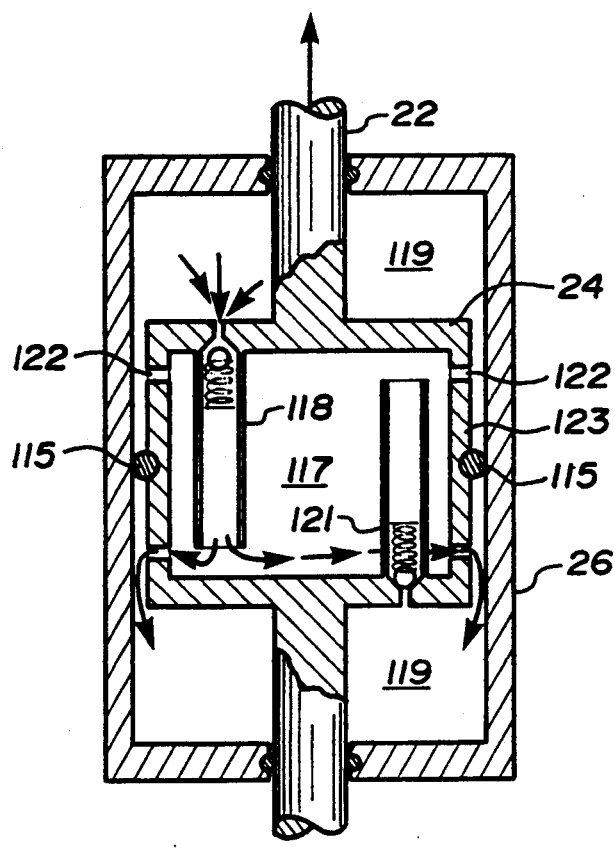
Figure 15:
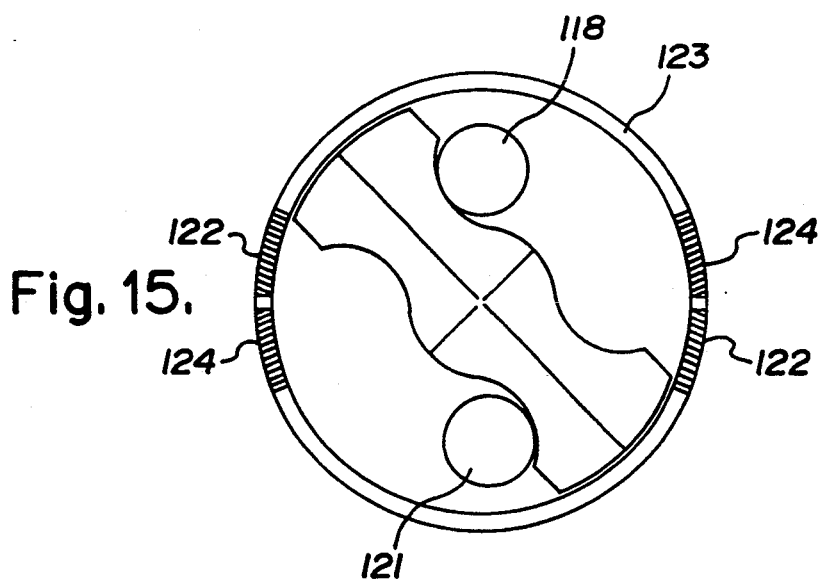
FIG. 15 is a simplified end view of the internals of the piston.
Figure 16:
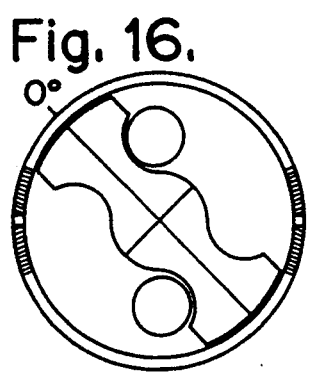
FIGS. 16–24 are views similar to FIG. 15, showing the valve in various positions.
Figure 17:
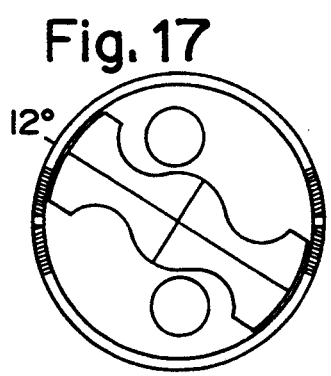
Figure 18:
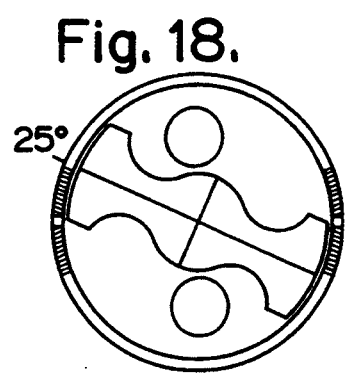
Figure 19:
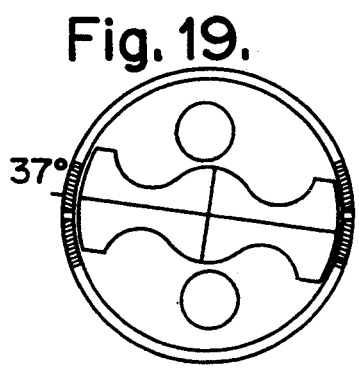
Figure 20:
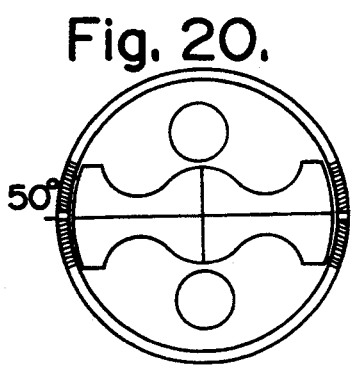
Figure 21:
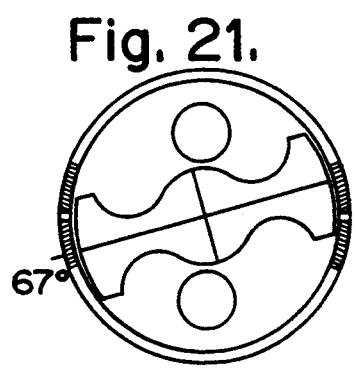
Figure 22:
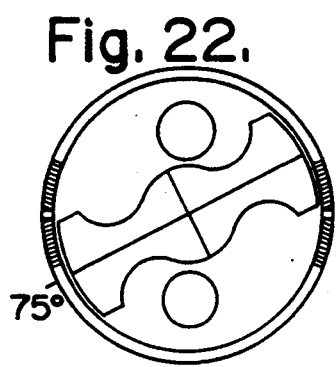
Figure 23:
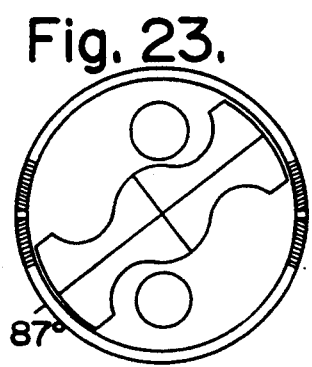
Figure 24:
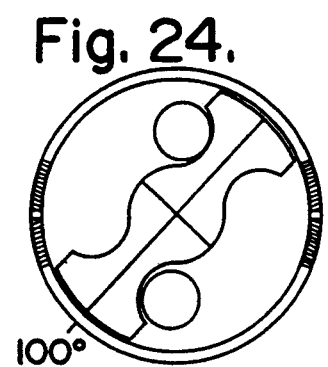

The piston 24 and cylinder 26 are shown in simplified form in FIGS. 13 and 14, with the fluid flows identified by arrows in each of flexion and extension.

The cylinder 26 is a closed or sealed unit and it is filled with hydraulic fluid. The piston 24 carries an external circumferential ring seal 115 for sealing against the side wall 105 of the cylinder 26.

The upper cap 113 of the piston 24 has an aperture 116 opening into the piston chamber 117. A spring-loaded one way check valve 118 controls the aperture 116 and allows pressurized hydraulic fluid to move downwardly from the upper end of the cylinder chamber 119 into the piston chamber 117.

The lower cap 114 of the piston 24 has an aperture 120 opening into the piston chamber 117. A spring-loaded one way check valve 121 controls the aperture 120 and allows pressurized fluid to move upwardly from the lower end of the cylinder chamber 119 into the piston chamber 117.

The check valves used are available from the Lee Company, Westbrook, Conn., under designation CKFA 2506205A.

A first pair of diametrically opposed flexion ports 122 extend through the piston side wall 123 at a point above the piston circumferential seal 115. A second pair of diametrically opposed extension ports 124 extend through the piston side wall 123 at a point below the circumferential seal 115.

From the foregoing and having reference to FIG. 13, when body weight acts downwardly on the push rod 22 and piston 24, with the flexion ports 122 open, hydraulic fluid may flow upwardly from the lower end of the cylinder chamber 119, through the lower check valve 121 into the piston chamber 117, out of the piston chamber through the flexion ports 122 and into the upper end of the cylinder chamber 119. Therefore, as long as the flexion ports 122 are open, the piston 24 may move downwardly, the damper B may contract and flexion of the knee joint may occur. If the flexion ports 122 are only partly open, there is damping or resistance to the knee rotation in flexion. If the flexion ports 122 are closed, the piston 24 is prevented from moving downwardly and the knee joint is locked against flexion.

Similarly, having reference to FIG. 14, when the push rod 22 and piston 24 are pulled upwardly, with the extension ports 124 open, pressurized hydraulic fluid may flow downwardly from the upper end of the cylinder chamber 119, through the upper check valve 118 into the piston chamber 117, out of the piston chamber through the extension ports 124 and into the lower end of the cylinder chamber 119. Therefore, as long as the extension ports 124 are open, the piston 24 may move upwardly, the damper B may extend and extension of the knee joint may occur. If the extension ports 124 are only partly open, there is damping or resistance to knee extension. If the ports 124 are closed, the piston 24 is prevented from moving upwardly and the knee joint is substantially locked against extension.

As previously stated, restriction of the fluid flow through the ports reduces the flow of fluid through the hollow piston, thereby controlling the rate of movement of the piston.

The rate of flow of the fluid is controlled by an adjustable rotatable valve 23. This valve 23 is illustrated in FIGS. 4 and 15–24. It comprises a shaft or rod 36 carrying a pair of lobes 125. The rod 36 extends axially and centrally into the piston chamber 117. It further extends upwardly through a bore 126 in the push rod 22 and is drivably connected with the servo motor 16 housed in the bracket 14.

The lobes 125 extend radially from the rod 36, substantially seal against the inside surface of the piston side wall 123 and each is adapted to extend vertically across both the upper flexion port 122 and the lower extension port 124 on one side of the piston 24.

The associated ports 122, 124 on each side of the piston 24 are circumferentially offset, as shown in FIGS. 16–24. Stated otherwise, the lower extension port 124 begins approximately where the upper flexion port 122 ends. The ports 122, 124 are narrow elongate horizontal slits. Typically they might have a length of 0.25 inches and width of 0.02 inches.

Therefore, there is a progressive nature to the reduction and subsequent increase in open area of a port as the valve lobe moves across it on a rotational travel. This of course affects the rate of fluid flow through the piston chamber 117 and determines the relative damping or resistance to rotation experienced by the knee joint.

By circumferentially offsetting the associated pair of upper and lower ports, there is a sequential and separate nature to the opening and closing of flexion and extension ports.

Stated otherwise, and as shown in FIGS. 16–24, the flexion and extension ports of an associated pair of ports on one side of the piston:

can each be separately progressively opened or closed; or each can be separately fully opened or closed; or one can be fully closed while the other is progressively closed; or both can be fully closed, and all of the foregoing can be accomplished with a single motor and valve, thereby assisting in achieving compactness and low weight.

The rotation of the inner valve 23 is determined by the software controlling a microprocessor 32, which in turn controls the servo motor 16.

Each step or movement of the prosthesis has been divided into segments (states), dependent on comparison of the incoming sensor signals and preset threshold values. Held in the memory of the microprocessor is a position signal for the inner valve 23. With each change from state to state the inner valve 23 position is altered, thus achieving a different knee joint control. For example, referring to FIG. 6A, state No. 1, the initial portion of stance phase, the inner valve 23 is set to allow fluid to escape from the flexion ports 122 and consequently the knee joint can bend as the amputee applies weight. The programmed computer monitors the increasing knee angle and when it reaches the stored threshold value that indicates that the knee has bent to the predetermined angle initiating state No. 2, then the position of the inner valve 23 is altered to completely restrict fluid flow from the flexion ports 122 and allow flow from the extension ports 124. This stops further knee joint bending and allows extension.

The above example illustrates that the assembly can have different control parameters depending on the direction of knee joint rotation (i.e. locked in flexion and allow extension). In other words, "simultaneous control". The fluid passes through separate ports for each of the two directions of knee movement. Therefore, if the flexion and extension ports are restricted independently of each other, the control of the rate of piston movement can be different for each direction.

The FIGS. 16–24 show discrete positions for the inner valve 23. In fact the positioning of the inner valve can be set at any position from 0 to 100 degrees, thus obtaining virtually an infinite range of knee joint damping. This is desirable for "tuning" the leg in activities such as stair descending, where the rate of descent must appeal to the amputee.

The microprocessor 32 used is available from Motorola Semiconductors Ltd. under designation XC 68 HC 811 E2 FN. This is an 8 bit processor having 2K of memory, 8 analog to digital convertors, and 8 digital inputs. The chip is about 1"×1" and there is no need for any other peripheral chips, thereby allowing it to fit into a small package within the prosthesis A.

The knee angle and load sensor signals are amplified and then fed directly into the microprocessor 32. The amplifiers 126, 127 used for knee angle and load signal conditioning are available from Texas Instruments under designations TLC 272 and TLC 274 respectively.

As shown, the amplifiers 126, 127 and microprocessor 32 are mounted on a circuit board 20 and are enclosed together with a battery 34 (Motorola SNN 4038A) and battery holder 33 in a shell 19 which is secured to the frame 4.

SOFTWARE

The software is set forth in the flow chart and attached Appendix.

Various sets of rules, or states, have been developed, one sets for each event (for example, level walking, sit down, stairs). Only one rule can be satisfied at one time, being satisfied only after the emitted signals have met the state conditions for the rule. The rules are arranged in such a way as to keep track of the position of the position of the AKP throughout each event.

The outcome of a rule being satisfied is the re-positioning of the actuating means.

The software can thus be considered to be "rule-based".

Due to the similarities of the sensor information during the course of each step from one step to another (repetitiveness) it is possible to determine the amplitude of each of the two signals at transition points during each step. These transition points are important times when the damping of the knee joint should be altered to allow the amputee to walk. The transition points are detected by the processor 32 by comparing the predetermined "threshold" values, stored in memory, with the real signals from the prosthesis A and cycling through the transition points as they occur. As long as the amputee continues to produce signals as expected, the processor can keep track of the cycle.

With this type of software in operation the hydraulic damper B can be adjusted as each transition point occurs, to a new position which was predetermined during fitting.

This system can therefore determine the position of the prosthesis A during the course of each step and apply an appropriate damping coefficient to the knee joint. Furthermore it is possible to detect whether the amputee is walking on level ground, down stairs, sitting down or has encountered a dangerous situation such as the toe of the prosthesis hitting the ground during swing phase (toe stubbing).

Level Ground

Figure 6A:
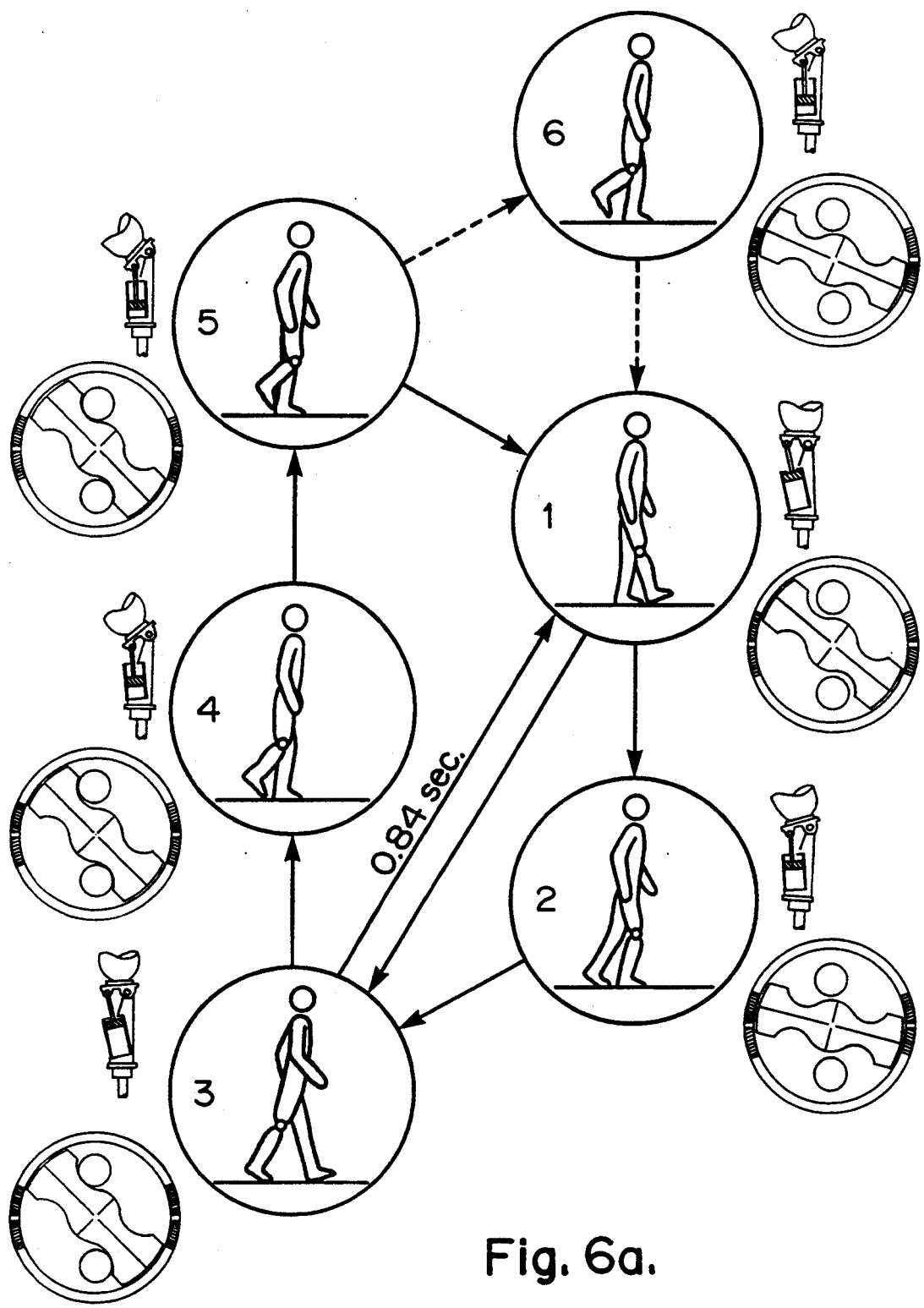
FIG. 6a is a diagram showing the states in level walking and correlating them with leg action, piston position and valve position.

FIG. 6A illustrates the point. Each of the numbered circles are referred to as states. The processor always begins in state #1 where the step begins. As the amputee applies weight to the prosthesis A the knee joint begins to bend. This increases the knee angle signal which is continuously being compared to a preset threshold value and as it equals or exceeds the threshold value the processor cycles to state #2. The hydraulic damper setting is altered at the transition point to predetermined settings to allow knee flexion while in state #1 and to lock knee flexion while in state #2.

During state #1 the damper's function is to damp knee flexion and simultaneously allow knee extension and during state #2 to lock knee flexion and simultaneously allow but damp knee extension. Note that the flexion damping has gone from a damped setting to a locked setting independent of the damped knee extension setting. This design allows the amputee to straighten the knee during state #2 even though the knee flexion is still locked.

The damped setting is required to control the rate of knee extension as the amputee proceeds. If a free extension setting was chosen the knee would "snap" straight giving the amputee a noticeably abnormal gait.

The initial knee flexion after heel contact and the straightening of the knee is found in normal gait patterns and is referred to as "knee bounce".

The exact mechanics as to how the hydraulic damper functions is shown in FIG. 6A beside each numbered circle.

Figure 7:
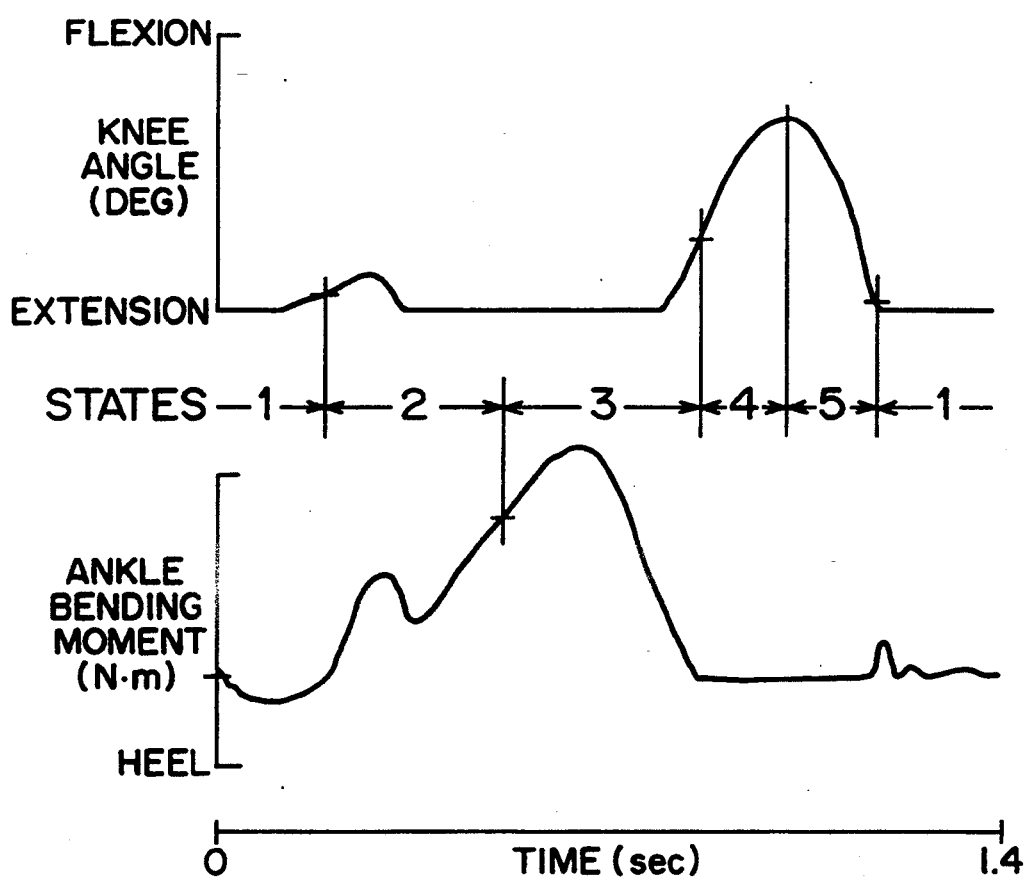
FIG. 7 is a plot showing the relationship between knee angle and strain (ankle bending moment) signals, related to the states, for level walking.
Figure 7A:
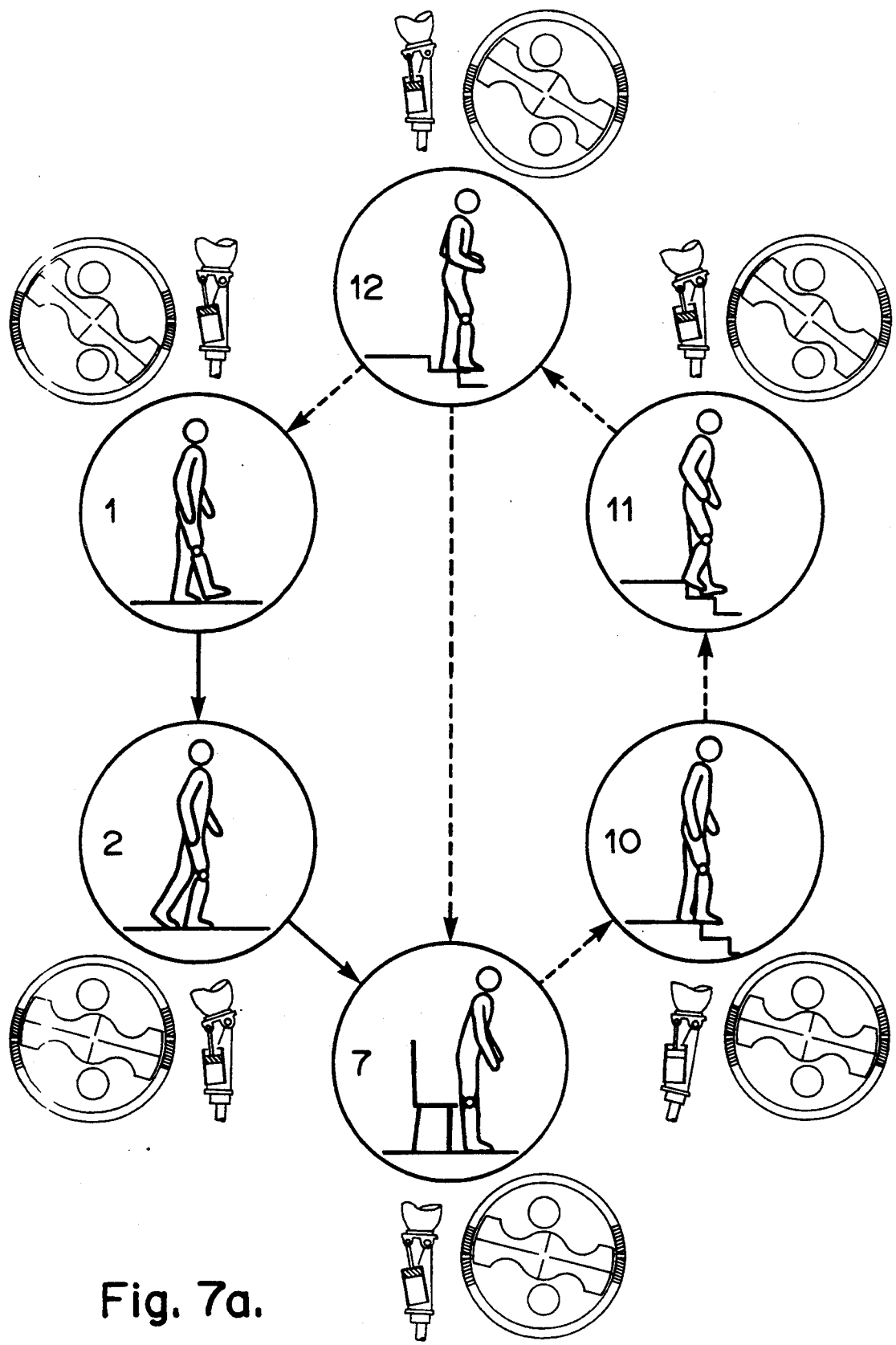
FIG. 7a is a diagram showing the states in stair descent and correlating them with leg action, piston position and valve position.

FIGS. 6 and 7 show the rules used for the comparison and the actual values of the output of the sensors expected for one step. Following through the step it can be seen that the transition from state #1 to state #2 occurs as the knee angle signal in FIG. 7 increases.

The graph shows that knee flexion stops shortly after the transition to state #2. The time delay is the time required for the damper to change.

As the amputee proceeds through the step the next important event is swing phase (time while the foot 8 is off the ground). Indication of the oncoming swing phase can be detected by continuously monitoring the load signal and comparing it to a predetermined value.

As the centre of gravity of the amputee passes over the foot, weight is applied to the toe. The increase in the bending moment strain or load signal causes the processor to switch to state #3 as soon as the load signal is equal to or exceeds the predetermined threshold value. The damper is commanded to unlock the knee joint, thus allowing the amputee to initiate swing phase when ready.

The entire swing phase is tracked by the processor. The transition to state #4 occurs when the knee signal increases past a preset threshold value as the knee joint flexes during the initial portion of swing phase.

After state #4 the bending moment strain or load signal is ignored and the processor monitors the first derivative of knee angle. The derivative is an indication of the speed and direction of the knee rotation. As the knee joint reaches the maximum flexion during swing the derivative becomes zero and detection of this produces a switch, to state #5. Note that the same command for the damper is maintained throughout states #3–4–5, that is, free flexion and free extension which allows swing phase to be completed.

Completion of the swing phase is detected when the knee angle signal decreases past a preset threshold value to indicate that the knee joint has extended back to the straight position. The processor switches to state #1 and the entire process is repeated as long as the amputee continues to walk on level ground.

Emergency Swing Phase Recovery (Stubbing the Toe)

The normal repetitive pattern of knee angle and bending moment strain information causes the processor to cycle through state #'s 1–2–3–4–5–1 (see FIGS. 6 & 7). When the toe of the prosthesis has contacted an obstacle during the swing phase the pattern is different. The pattern is now 1–2–3–4–5–6–1. After state #5 the processor monitors the knee angle derivative information and switches to state #6 if the first derivative has become positive, indicating that the knee is no longer extending but is now flexing (i.e. the obstacle has interrupted the normal velocity of the knee extension). During state #6 the damper is instructed to lock the flexion of the knee joint.

Additional state changes exist for the level walking diagram. Circumduction is the completion of the swing phase without flexing the knee joint. This is done by swinging the limb sideways in an arc to clear the ground instead of flexing the knee. Without the flexion of the knee during the swing phase the processor would switch from state #'s 1–2–3 and stop. This problem is alleviated by measuring the time that the processor is in state #3 and if the knee has not been flexed in a predetermined amount of time the processor switches back to state #1 regardless of any inputs.

Sit Down Mode

During the daily events there are times when the amputee is sitting for an extended period of time. The knee joint of the prosthesis should be in an unlocked position for this time in order for the amputee to position the leg in any desired position. For instance he may wish to have it flexed to place the foot under a chair, or in a right angle position to sit upright, or in a partially flexed position for sitting in a car. The positioning is done by manipulating the prosthesis usually with the hands or the contralateral (other) foot.

Figure 8A:
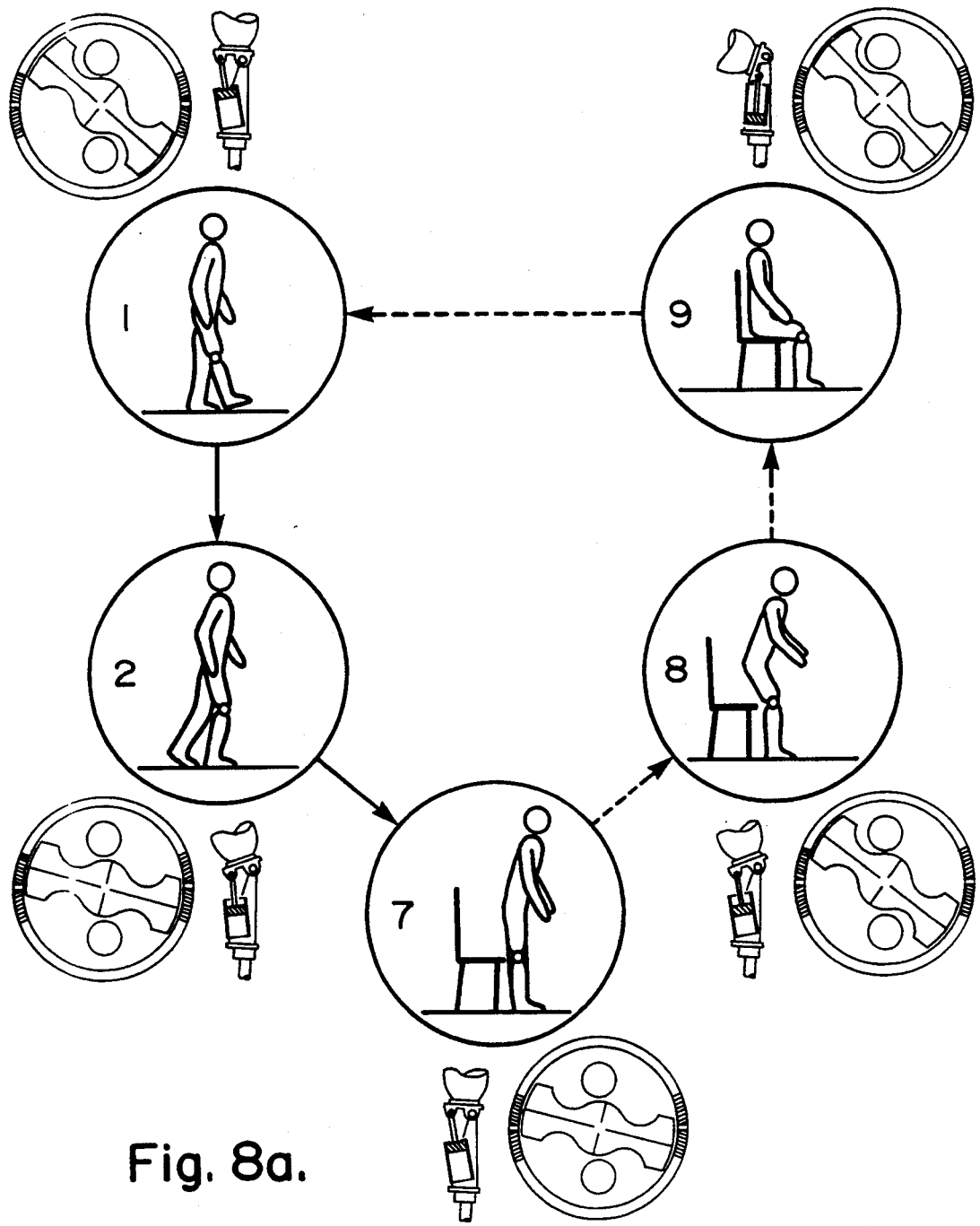
FIG. 8a is a diagram showing the states in sitting down and correlating them with leg action, piston position and valve position.
Figure 9:
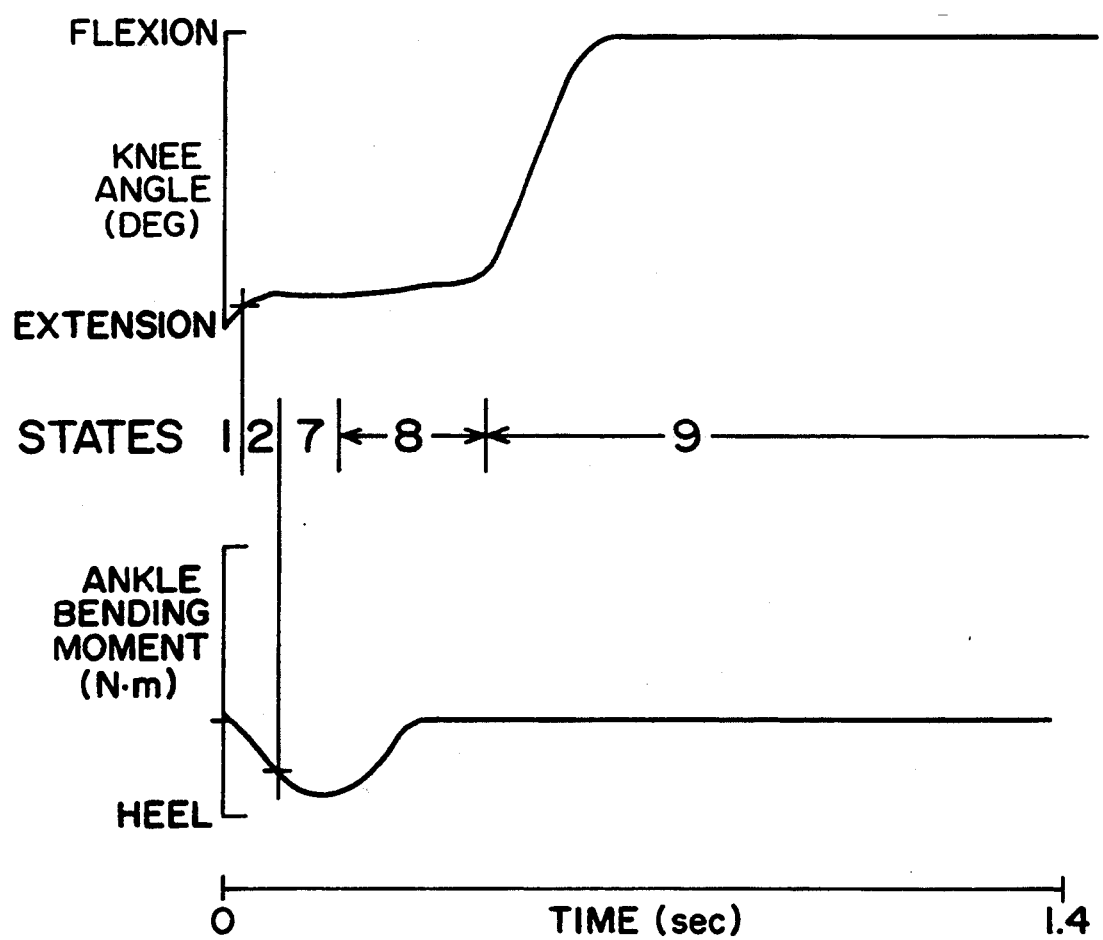
FIG. 9 is a plot showing the relationship between knee angle and strain signals, related to the states, for sitting down.

Sitting is accomplished by training the amputee to perform a certain move to instruct the processor of the attempt to sit down. FIGS. 8A and 8 show the cycle of states for sitting down. FIG. 9 shows the change in signals for a typical sit down motion. Initially the processor will be residing in state #1. The amputee leans backward which increases the load on the heel of the prosthesis and begins to flex the knee joint. The processor switches from state #1 to state #2 as the knee signal passes a preset threshold value (see state change on FIG. 9).

The load on the heel decreases the load signal past a preset threshold value and the processor switches to state #7. As soon as the processor switches to state #7, a timer starts and measures the time which the load is present on the heel. After ⅓ of a second the processor switches to state #8 which commands the damper to allow knee joint flexion. The amputee bears weight on the prosthesis and descends to the chair at a controlled rate. Measurement of time is again made and the processor switches to state #9 after ⅔ seconds. This commands the damper to be free in both flexion and extension of the knee joint, allowing the amputee to manipulate the leg to be comfortable in the seated position. The processor will remain in state #9 until the knee joint is extended to the straight position thus decreasing the knee angle signal past a threshold value at which the processor switches to state #1.

Stair Descending

The usual method for an amputee to descend stairs is to use only his good leg to lower his body weight down each stair until his prosthesis contacts the next stair. He then repeats the motion again using the good leg. The prosthesis is not used at all and the descent is "one stair at a time".

The second method is for the more agile amputee and consists of the normal "step over step" approach but doing so with the knee having uncontrolled descent as his weight flexes the knee (jack knifing).

The present invention incorporates a method of first detecting the fact that the amputee is about to descend a step and then offering a controlled rate of descent.

Figure 10:
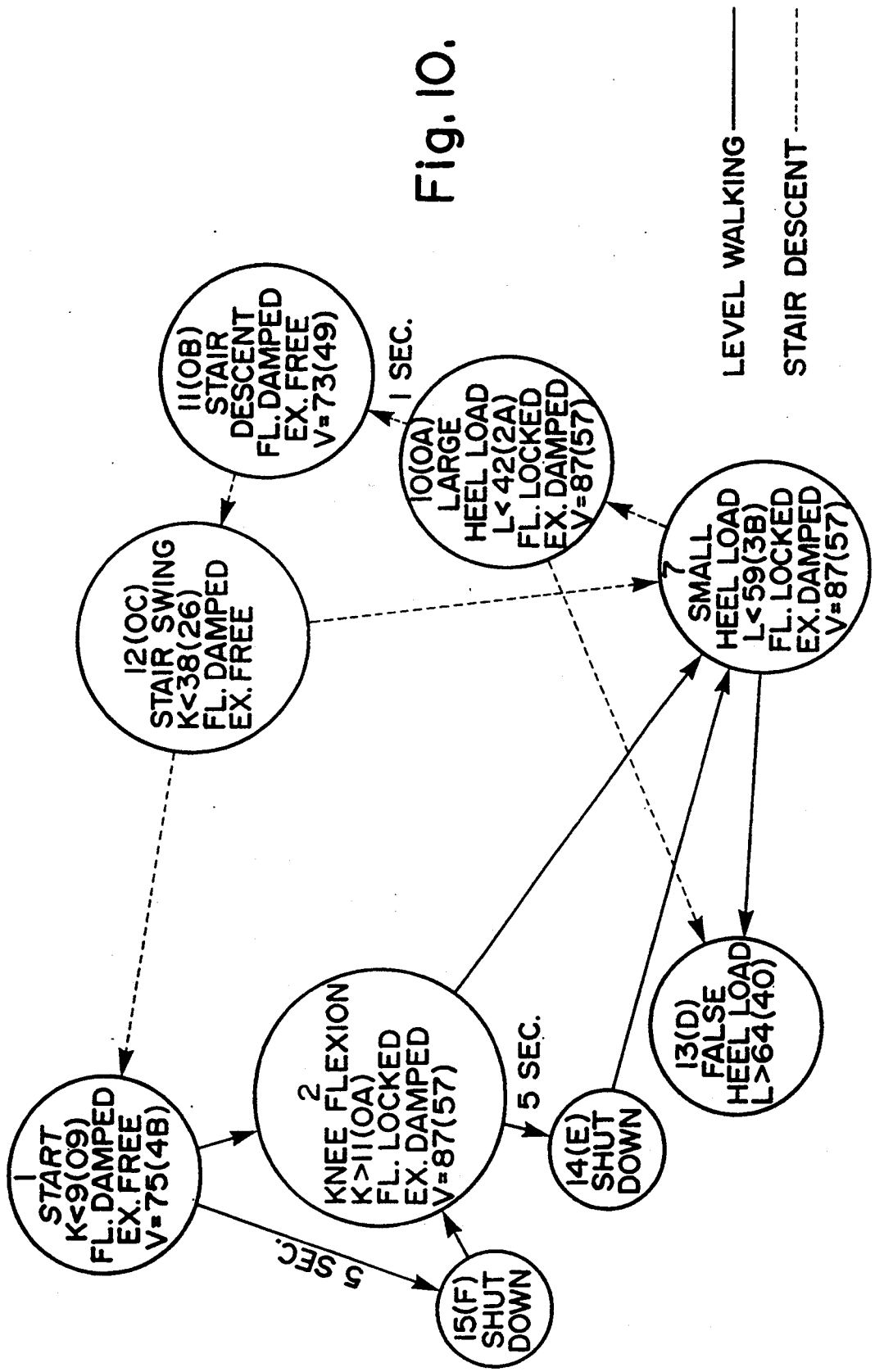
FIG. 10 is a diagram showing the states in stair descent, with the appropriate state conditions shown.
Figure 11:
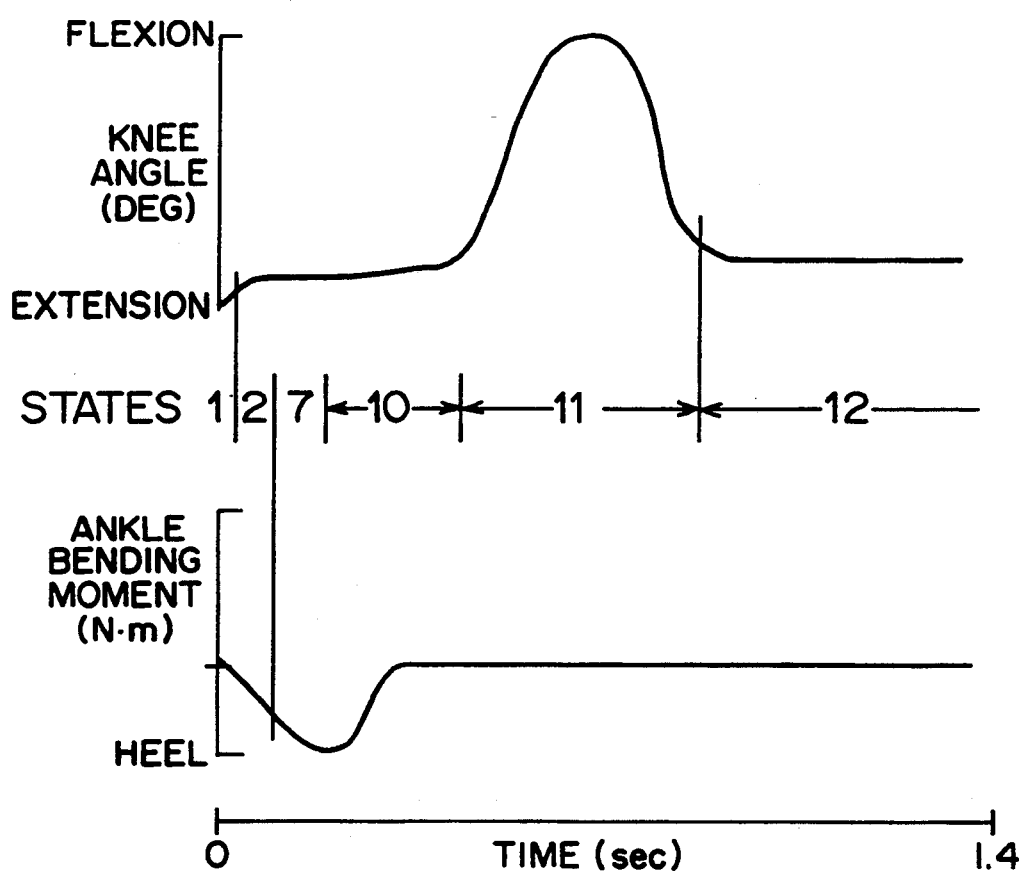
FIG. 11 is a plot showing the relationship between knee angle and strain signals, related to the states, for stair descent.

In order to initiate the descending of stairs, the processor must receive the appropriate signals from the user. This is done by placing the heel of the prosthesis on the edge of the stair and applying weight. Similar to level walking the first state change is from state #1 to state #2 as the knee begins to flex (see above). At this point the load signal decreases (heel loading) and the processor switches to state #7 and then to state #10 as the load reaches a preset threshold value (see FIGS. 10 & 11).

Note that the amount of weight placed on the heel by the user determines whether the processor stops at state #7 (detects "sit-down") or continues to state #10 (detects "stairs"). The user is trained to apply the appropriate weight to instruct the processor correctly.

A timer is started when the processor switches to state #10. As long as the user maintains the load for 1 second the processor will then switch to state #11. During state #11 the damper is commanded to damp the flexion of the knee joint and allow extension. This damping is similar to the hydraulic control unit on a door. The rate at which the door can swing is controlled by the hydraulic fluid within the cylinder. For the knee this damping is preset dependent on the wishes of the user. Some like to descend stairs at a slow rate while others prefer a fast descent.

At completion of each stair the user descends the next step on his contralateral (other) limb. During this time the processor is waiting for the knee joint to extend during the swing phase. The extension reduces the knee signal past a preset threshold value and the processor switches to state #12. The damper is commanded to lock flexion and allow extension. The user again places the heel on the next stair and repeats the sequence 7-1-0-11-12 for each step. Note that the processor does not return to state #1 after each step. This is due to the lack of a complete extension of the leg prior to the next step.

Once the flight of stairs has been completed, the knee joint is extended to the straight position and the processor switches to state #1 as the knee angle is reduced to a preset threshold value. The choice between stairs, sit down or level walking is now available.

Figure 12:
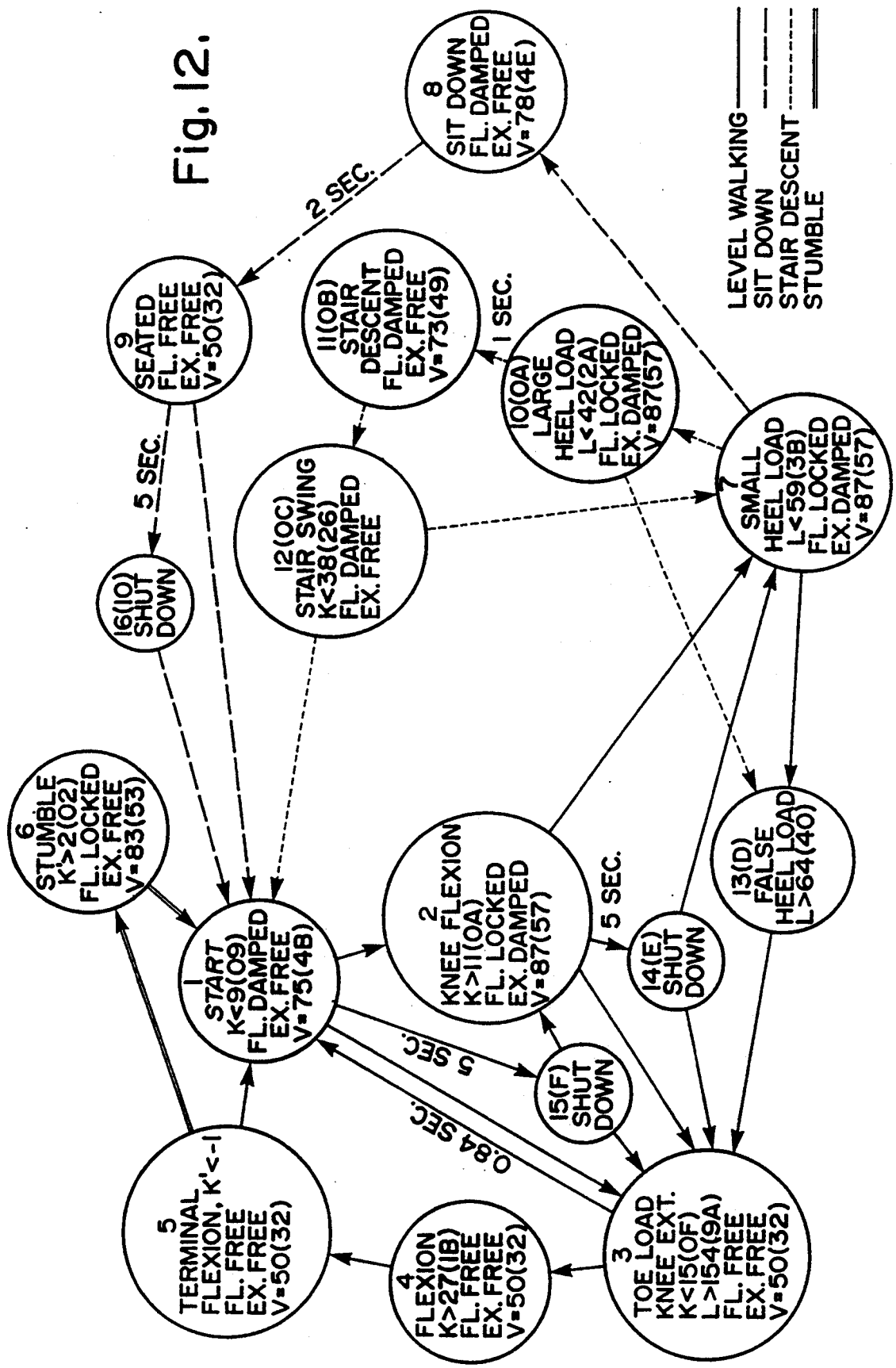
FIG. 12 is a comprehensive diagram showing the states and conditions for the various modes of action.
Figure 12A:
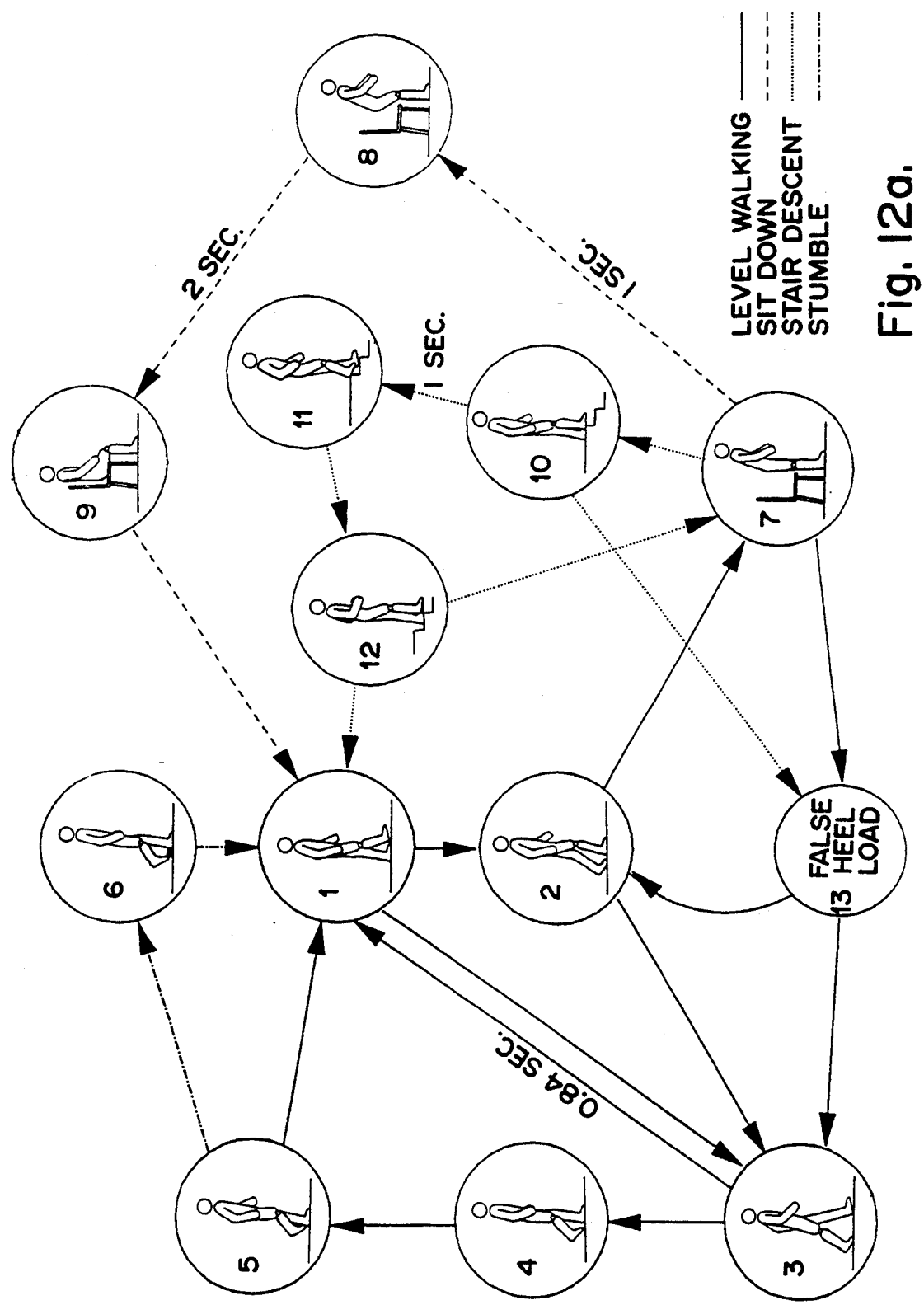
FIG. 12a is a comprehensive diagram corresponding with FIG. 12 and showing the various body actions.

FIG. 12 shows all of the states grouped together. At the beginning of each step the value-based software detects whether the amputee is proceeding on level ground (state #'s 1-2-3-4-5-1), has stubbed the toe during a step on level ground (1-2-3-4-5-6-1), is sitting down (1-2-7-8-9-1) or is descending stairs (1-2-7-1-0-11-12).

The amputee need not push any buttons or turn any levers to instruct the processor to change functions for different terrains. Detection is automatically done in real time dependent on the movements of the amputee.

Additional features of the state diagram include a battery life saver. If the amputee stops for more than 3 seconds in states 1, 2 or 9 the processor stops powering the control motor and goes to a shutdown state.

A low battery warning beeper signals the user that battery replacement is required. In the event that the battery is completely depleted the damper is commanded to damp flexion and free extension prior to complete loss of power. This allows the amputee to still bear weight on the leg without excessive knee flexion until a charged battery is placed in leg. As the flexion is damped the swing phase must be accomplished by circumduction during this time.

The embodiments of the invention in which an exclusive property or privilege is claimed are defined as follows:

1. In an above knee prosthesis (AKP) for use by a human user, said AKP having upper and lower leg segments, a knee joint connecting the segments and a foot attached to the lower segment, the improvement comprising:

a hydraulic damper means, pivotally connected with the leg segments for separately and variably damping each of flexion and extension rotational movements of the knee joint throughout the stance and swing phases of gait utilizing restriction of hydraulic fluid flow;

said damper means comprising a cylinder, forming an internal chamber, and a piston adapted to slide therein, said piston engaging the cylinder in sealed relationship and dividing the chamber into first and second end chambers filled with hydraulic fluid when in use, said piston being operative to reciprocate within the cylinder chamber as the leg segments move together in flexion or separate in extension, said damper means having first and second passageways, each connecting the end chambers, said damper means having first variable valve means associated with the first passageway for regulating fluid flow therethrough and second variable valve means associated with the second passageway for regulating fluid flow therethrough, said damper means having first one way check valve means for enabling fluid to flow between end chambers through the first passageway when the leg segments endeavor to separate in extension and second one way check valve means for enabling fluid to flow between end chambers through the second passageway when the leg segments endeavor to move together in flexion;

actuating means for adjusting each of the first and second variable valve means so the flow capacity of each of the first and second passageways may be separately varied;

electronic sensing means for continuously monitoring AKP knee angle and emitting signals representative thereof, electronic sensing means for continuously monitoring position of the center of gravity of the user's body relative to the AKP foot and emitting signals representative thereof; and programmed computer means for receiving the emitted signals, continuously establishing from said signals the state of the AKP throughout the course of gait and activating the actuating means to separately vary the flow capacity of one or both passageways at appropriate transition points between AKP states throughout the stance and swing phases of gait.

2. The improvement as set forth in claim 1 wherein the means for monitoring position of the center of gravity of the user's body comprises means for sensing lower leg bending moment strain.

3. The improvement as set forth in claim 2 comprising:

a third passageway connecting the first and second passageways between the check valve means and variable valve means of each passageway.

4. The improvement as set forth in claim 2 wherein:
the cylinder has side and end walls;
the piston is cylindrical and hollow, having end walls and a side wall forming a piston chamber, said piston side wall carrying an exterior circumferential seal ring for sealing against the cylinder side wall;
the piston forms a first aperture on one side of the seal ring, which aperture connects the piston chamber with the first cylinder end chamber;
the piston forms a second aperture on the other side of the seal ring, which second aperture connects the piston chamber with the second cylinder end chamber;
the first one way check valve means is connected with the first aperture and is operative to allow fluid to flow between the cylinder first end chamber and the piston chamber in extension;
the second one way check valve means is connected with the second aperture and is operative to allow fluid to flow between the cylinder second end chamber and the piston chamber in flexion;
the piston second passageway including a first pair of diametrically opposed ports connecting the piston chamber with the cylinder first end chamber;
the first passageway including a second pair of diametrically opposed ports connecting the piston chamber with the cylinder second end chamber;
the piston is associated with first valve means for progressively reducing or increasing the area of the first pair of ports which is available for fluid flow and with second valve means for separately progressively reducing or increasing the area of the second pair of ports which is available for fluid flow;
so that the first aperture, first check valve means, piston chamber and second pair of ports form the first passageway, said first check valve means being operative to route flow therethrough in extension, said second valve means and second pair of ports combining to provide the first variable valve means for regulating fluid flow therethrough;
so that the second aperture, second check valve means, piston chamber and first pair of ports form the second passageway, said second check valve means being operative to route flow therethrough in flexion, said first valve means and first pair of ports combining to provide the second variable valve means for regulating fluid flow therethrough; and
so that the piston chamber connects the first and second passageways between the check valve means and the ports of each of the first and second passageways.

5. The improvement as set forth in claim 4 wherein:
each of the ports is a slit extending circumferentially of the piston and the second pair of ports is offset circumferentially relative to the first pair of ports; and
the valve means is a rotatable plug adapted to progressively cover or uncover the first and second slit ports.

6. The improvement as set forth in claims 1, 2, 3, 4 or 5 wherein:
the programmed computer means is adapted to compare the emitted signals against stored threshold values indicative of transition points between states of a repetitive movement of the AKP and, when the signals substantially correlate with the threshold values, to vary flow capacity of one or both of the passageways.

* * * * *